United States Patent [19]

Ruggeri et al.

[11] Patent Number: 5,900,476
[45] Date of Patent: May 4, 1999

[54] THERAPEUTIC DOMAINS OF VAN WILLEBRAND FACTOR

[75] Inventors: Zaverio M. Ruggeri, La Jolla; Jerry L. Ware, Encinitas, both of Calif.

[73] Assignee: The Scripps Research Institute, La Jolla, Calif.

[21] Appl. No.: 07/841,591

[22] Filed: Feb. 26, 1992

Related U.S. Application Data

[63] Continuation-in-part of application No. PCT/US91/07756, Oct. 17, 1991, and a continuation-in-part of application No. 07/613,004, Nov. 13, 1990, abandoned, and application No. 07/600,183, Oct. 17, 1990, abandoned, said application No. 07/613,004, is a continuation-in-part of application No. 07/600,183, which is a continuation-in-part of application No. 07/519,606, May 7, 1990, Pat. No. 5,238,919, which is a continuation-in-part of application No. 07/270,488, Nov. 4, 1988, abandoned, which is a continuation of application No. 06/869,188, May 30, 1986, abandoned.

[51] Int. Cl.⁶ .................. C07K 14/745; C12N 15/12; A61K 38/36
[52] U.S. Cl. .................. 530/380; 530/829; 536/23.5; 514/822
[58] Field of Search .................. 514/2, 12, 22, 514/822; 530/350, 380, 829; 536/23.5; 435/69.6

[56] References Cited

U.S. PATENT DOCUMENTS

| | | | |
|---|---|---|---|
| 4,518,584 | 5/1985 | Mark et al. | 424/85 |
| 4,959,314 | 9/1990 | Merk et al. | 435/69.1 |

FOREIGN PATENT DOCUMENTS

| | | |
|---|---|---|
| 0 255 206 | 2/1988 | European Pat. Off. . |
| WO 91/13093 | 9/1991 | WIPO . |

OTHER PUBLICATIONS

Bonthron, D. et al. *Nucl. Acids Res.*, 14(17), 7125–7127 (1986).
Fujimura, Y. et al. *J. Biol. Chem.*, 261(1), 381–385 (1986).
Fujimura, Y. et al., *J. Biol. Chem.*, 262, 1734–1739 (1987).
Ware, J. et al., *Proc. Natl. Acad. Sci. USA*, 88, 2946–2950 (1991).
Read, et al. *Proc. Natl. Acad. Sci.*, 75, 4514–4518 (1978).
Cooney, K.A. et al., *Blood*, 76 (supp. 1) Abstract 1661, p. 418a, Nov. 15, 1990.
Gralnick, H.R. et al., *Oral Communications on von Willebrand Factor–Ib Interaction* presented at meeting in Amsterdam, the Netherlands, Abstract 536, p. 840, Jul. 5, 1991.
Mancuso, D.J. et al. *J. Biol. Chem.*, 264(33), 19514–19527, Table V, (1989).
Andrews, R.K. et al., *Biochemistry*, 28, 8317–8326 (1989).
Lynch, D.C. et al., *Cell*, 41, 49–56 (1985).
Handa, M. et al., *J. Biol. Chem.*, 261(27), 12579–12585 (1986).
Azuma, H. et al., *J. Biol. Chem.*, 266(19), 12342–12347 (1991).
Mohri, H. et al., *J. Biol. Chem.*, 263(34), 17901–17904 (1988).
Hanahan, D., *J. Mol. Biol.*, 166, 557–580 (1983).
Vicente, V. et al., *J. Biol. Chem.*, 265, 274–280 (1990).
Sugimoto, M. et al., *Biochemistry*, 30(21), 5202–17 (1991).
Rosenberg, A.H. et al., *Gene*, 56, 125–136 (1987).
Newman, P.J. et al. *J. Clin. Invest.*, 82, 739–743 (1988).
Kunkel, T.A., *Proc. Natl. Acad. Sci. USA*, 82, 488–492 (1985).
Fulcher, C.A. et al. *Proc. Natl. Acad. Sci. USA*, 79, 1648–1652 (1982).
Craik, C. "Use of Oligonucleotides for site Specific Mutagenesis", *Biotechniques*, Jan./Feb. 1985 at p. 12.
Mohri et al. "Isolation of the von Willebrand . . . " JBC Oct. 15, 1989 vol. 264, pp. 17361–17367.
Lerner "Tapping the immunization . . . " No date 799 Oct. 14, 1982 pp. 592–595.

*Primary Examiner*—Dian C. Jacobson
*Assistant Examiner*—Hyo Kim
*Attorney, Agent, or Firm*—Synnestvedt & Lechner

[57] ABSTRACT

A polypeptide which is capable of inhibiting binding of von Willebrand factor (vWF) to platelets and comprising an amino acid sequence that corresponds to the amino acid sequence of that fragment of mature von Willebrand factor subunit having its amino terminus at about $Cys^{509}$ and its carboxy terminus at about $Cys^{695}$, said polypeptide comprising optionally a second and/or a third domain, the second domain corresponding to the amino acid sequence of that fragment of mature vWF subunit having its amino terminus at about $Thr^{450}$ and its carboxy terminus at about $Tyr^{508}$, or a subfragment or combination of subfragments thereof, and a third domain corresponding to the amino acid sequence of that fragment of mature vWF subunit having its amino terminus at about $Asp^{696}$ and its carboxy terminus at about $Gly^{727}$, or a subfragment or combination of subfragments thereof; and also a process for producing said polypeptides from encoding DNA sequences, and also a method of inhibiting or treating thrombosis in a patient which comprising administering to such patient an effective amount of a therapeutic composition comprising one or more polypeptides of the invention.

11 Claims, 4 Drawing Sheets

FIG.1A

```
GAA-GAC-TGT-CCA-GTG-TGT-GAG-GTG-GCT-GGC-CGG-CGT-TTT-GCC-TCA-GGA-AAG-AAA-GTC-ACC-
Glu Asp Cys Pro Val Cys Glu Val Ala Gly Arg Arg Phe Ala Ser Gly Lys Lys Val Thr
                    440                           450

TTG-AAT-CCC-AGT-GAC-CCT-GAG-CAC-TGC-CAG-ATT-TGC-CAC-TGT-GAT-GTT-GTC-AAC-CTC-ACC-
Leu Asn Pro Ser Asp Pro Glu His Cys Gln Ile Cys His Cys Asp Val Val Asn Leu Thr
                    460                           470

TGT-GAA-GCC-TGC-CAG-GAG-CCG-GGA-GGC-CTG-GTG-GTG-CCT-CCC-ACA-GAT-GCC-CCG-GTG-AGC-
Cys Glu Ala Cys Gln Glu Pro Gly Gly Leu Val Val Pro Pro Thr Asp Ala Pro Val Ser
                    480                           490

CCC-ACC-ACT-CTG-TAT-GTG-GAG-GAC-ATC-TCG-GAA-CCG-CCG-TTG-CAC-GAT-TTC-TAC-TGC-AGC
Pro Thr Thr Leu Tyr Val Glu Asp Ile Ser Glu Pro Pro Leu His Asp Phe Tyr Cys Ser
                    500                           510

AGG-CTA-CTG-GAC-CTG-GTC-TTC-CTG-CTG-GAT-GGC-TCC-TCC-AGG-CTG-TCC-GAG-GCT-GAG-TTT-
Arg Leu Leu Asp Leu Val Phe Leu Leu Asp Gly Ser Ser Arg Leu Ser Glu Ala Glu Phe
                    520                           530

GAA-GTG-CTG-AAG-GCC-TTT-GTG-GTG-GAC-ATG-ATG-GAG-CGG-CTG-CGC-ATC-TCC-CAG-AAG-TGG
Glu Val Leu Lys Ala Phe Val Val Asp Met Met Glu Arg Leu Arg Ile Ser Gln Lys Trp
                    540                           550

GTC-CGC-GTG-GCC-GTG-GTG-GAG-TAC-CAC-GAC-GGC-TTC-CAC-GCC-TAC-ATC-GGG-CTC-AAG-GAC-
Val Arg Val Ala Val Val Glu Tyr His Asp Gly Phe His Ala Tyr Ile Gly Leu Lys Asp
                    560                           570

CGG-AAG-CGA-CCG-TCA-GAG-CTG-CGG-CGC-ATT-GCC-AGC-CAG-GTG-AAG-TAT-GCG-GGC-AGC-CAG
Arg Lys Arg Pro Ser Glu Leu Arg Arg Ile Ala Ser Gln Val Lys Tyr Ala Gly Ser Gln
                    580                           590
```

FIG.1B

```
GTG-GCC-TCC-ACC-GAG-GTC-TTG-AAA-TAC-ACA-CTG-TTC-CAA-ATC-TTC-AGC-AAG-ATC-GAC-
Val Ala Ser Thr Glu Val Leu Lys Tyr Thr Leu Phe Gln Ile Phe Ser Lys Ile Asp
                                600                                        610

CGC-CCT-GAA-GCC-TCC-CGC-ATC-GCC-CTG-CTC-CTG-ATG-GCC-AGC-CAG-GAG-CCC-CAA-CGG-ATG
Arg Pro Glu Ala Ser Arg Ile Ala Leu Leu Leu Met Ala Ser Gln Glu Pro Gln Arg Met
                                620                                        630

TCC-CGG-AAC-TTT-GTC-CGC-TAC-GTG-CAG-GGC-CTG-AAG-AAG-AAG-GTC-ATT-GTG-ATC-CCG-
Ser Arg Asn Phe Val Arg Tyr Val Gln Gly Leu Lys Lys Lys Val Ile Val Ile Pro
                                640                                        650

GTG-GGC-ATT-GGG-CCC-CAT-GCC-AAG-CTC-CGC-CTC-ATC-GAG-AAG-CAG-GCC-CCT
Val Gly Ile Gly Pro His Ala Asn Leu Lys Gln Ile Arg Leu Ile Glu Lys Gln Ala Pro
                                660                                        670

GAG-AAC-AAG-GCC-TTC-GTG-CTG-AGC-AGT-GTG-GAT-GAG-CTG-GAG-CAG-CAA-AGG-GAC-GAG-ATC-
Glu Asn Lys Ala Phe Val Leu Ser Ser Val Asp Glu Leu Glu Gln Gln Arg Asp Glu Ile
                                680                                        690

GTT-AGC-TAC-CTC-TGT-GAC-CTT-GCC-CCT-GAA-GCC-CCT-CCT-CCT-ACT-CTG-CCC-CCC-CAC-ATG
Val Ser Tyr Leu Cys Asp Leu Ala Pro Glu Ala Pro Pro Pro Thr Leu Pro Pro His Met
                                700                                        710

GCA-CAA-GTC-ACT-GTG-GGC-CCG-GGG-CTC-TTG-GGG-GTT-TCG-ACC-CTG-GGG-CCC-AAG-AGG-AAC-
Ala Gln Val Thr Val Gly Pro Gly Leu Leu Gly Val Ser Thr Leu Gly Pro Lys Arg Asn
                                720                                        730

TCC-ATG-GTT-CTG-GAT-GTG-GCG-TTC-GTC-CTG-GAA-GGA-TCG-GAC-AAA-ATT-GGT-GAA-GCC-GAC
Ser Met Val Leu Asp Val Ala Phe Val Leu Glu Gly Ser Asp Lys Ile Gly Glu Ala Asp
                                740                                        750
```

| DESIGNATION | SEQUENCE | REACTIVITY WITH NMC-4 (DOT BLOT) |
|---|---|---|
| rvWF 441-733 | 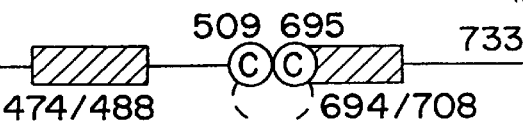 | + |
| rvWF 492-733 | 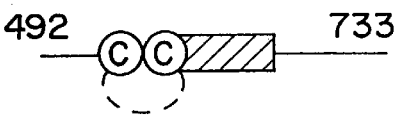 | + |
| rvWF 508-733 |  | + |
| rvWF 441-704 | 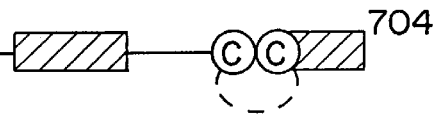 | + |
| rvWF 441-700 |  | + |
| rvWF 441-696 | 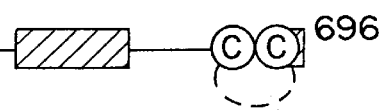 | − |
| rvWF 508-704 |  | ± |
| rvWF 508-696 |  | − |
FIG. 2

SEQUENCE LISTING (1) GENERAL INFORMATION:

(iii) NUMBER OF SEQUENCES: 15

(2) INFORMATION FOR SEQ ID NO: 1:

(i) SEQUENCE CHARACTERISTICS:
      (A) LENGTH: 960
      (B) TYPE: Nucleic Acid
      (C) STRANDEDNESS: single stranded
      (D) TOPOLOGY: Linear (xi) SEQUENCE DESCRIPTION: SEQ ID NO: 1:

```
GAA GAC TGT CCA GTG TGT GAG GTG GCT GGC                                 30
Glu Asp Cys Pro Val Cys Glu Val Ala Gly
                435                 440

CGG CGT TTT GCC TCA GGA AAG AAA GTC ACC                                 60
Arg Arg Phe Ala Ser Gly Lys Lys Val Thr
                445                 450

TTG AAT CCC AGT GAC CCT GAG CAC TGC CAG                                 90
Leu Asn Pro Ser Asp Pro Glu His Cys Gln
                455                 460

ATT TGC CAC TGT GAT GTT GTC AAC CTC ACC                                120
Ile Cys His Cys Asp Val Val Asn Leu Thr
                465                 470

TGT GAA GCC TGC CAG GAG CCG GGA GGC CTG                                150
Cys Glu Ala Cys Gln Glu Pro Gly Gly Leu
                475                 480

GTG GTG CCT CCC ACA GAT GCC CCG GTG AGC                                180
```

|  |  |
|---|---|
| Val Val Pro Pro Thr Asp Ala Pro Val Ser<br>485                       490 |  |
| CCC ACC ACT CTG TAT GTG GAG GAC ATC TCG<br>Pro Thr Thr Leu Tyr Val Glu Asp Ile Ser<br>                  495                  500 | 210 |
| GAA CCG CCG TTG CAC GAT TTC TAC TGC AGC<br>Glu Pro Pro Leu His Asp Phe Tyr Cys Ser<br>                  505                  510 | 240 |
| AGG CTA CTG GAC CTG GTC TTC CTG CTG GAT<br>Arg Leu Leu Asp Leu Val Phe Leu Leu Asp<br>                  515                  520 | 270 |
| GGC TCC TCC AGG CTG TCC GAG GCT GAG TTT<br>Gly Ser Ser Arg Leu Ser Glu Ala Glu Phe<br>                  525                  530 | 300 |
| GAA GTG CTG AAG GCC TTT GTG GTG GAC ATG<br>Glu Val Leu Lys Ala Phe Val Val Asp Met<br>                  535                  540 | 330 |
| ATG GAG CGG CTG CGC ATC TCC CAG AAG TGG<br>Met Glu Arg Leu Arg Ile Ser Gln Lys Trp<br>                  545                  550 | 360 |
| GTC CGC GTG GCC GTG GTG GAG TAC CAC GAC<br>Val Arg Val Ala Val Val Glu Tyr His Asp<br>                  555                  560 | 390 |
| GGC TTC CAC GCC TAC ATC GGG CTC AAG GAC<br>Gly Ser His Ala Tyr Ile Gly Leu Lys Asp<br>                  565                  570 | 420 |
| CGG AAG CGA CCG TCA GAG CTG CGG CGC ATT<br>Arg Lys Arg Pro Ser Glu Leu Arg Arg Ile<br>                  575                  580 | 450 |
| GCC AGC CAG GTG AAG TAT GCG GGC AGC CAG<br>Ala Ser Gln Val Lys Tyr Ala Gly Ser Gln<br>                  585                  590 | 480 |
| GTG GCC TCC ACC AGC GAG GTC TTG AAA TAC<br>Val Ala Ser Thr Ser Glu Val Leu Lys Tyr<br>                  595                  600 | 510 |
| ACA CTG TTC CAA ATC TTC AGC AAG ATC GAC<br>Thr Leu Phe Gln Ile Phe Ser Lys Ile Asp<br>                  605                  610 | 540 |
| CGC CCT GAA GCC TCC CGC ATC GCC CTG CTC<br>Arg Pro Glu Ala Ser Arg Ile Ala Leu Leu<br>                  615                  620 | 570 |
| CTG ATG GCC AGC CAG GAG CCC CAA CGG ATG<br>Leu Met Ala Ser Gln Glu Pro Gln Arg Met<br>                  625                  630 | 600 |
| TCC CGG AAC TTT GTC CGC TAC GTC CAG GGC<br>Ser Arg Asn Phe Val Arg Tyr Val Gln Gly<br>                  635                  640 | 630 |
| CTG AAG AAG AAG AAG GTC ATT GTG ATC CCG<br>Leu Lys Lys Lys Lys Val Ile Val Ile Pro<br>                  645                  650 | 660 |
| GTG GGC ATT GGG CCC CAT GCC AAC CTC AAG<br>Val Gly Ile Gly Pro His Ala Asn Leu Lys<br>                  655                  660 | 690 |
| CAG ATC CGC CTC ATC GAG AAG CAG GCC CCT<br>Gln Ile Arg Leu Ile Glu Lys Gln Ala Pro<br>                  665                  670 | 720 |
| GAG AAC AAG GCC TTC GTG CTG AGC AGT GTG<br>Glu Asn Lys Ala Phe Val Leu Ser Ser Val<br>                  675                  680 | 750 |
| GAT GAG CTG GAG CAG CAA AGG GAC GAG ATC | 780 |

```
Asp Glu Leu Glu Gln Gln Arg Asp Glu Ile
            685                 690

GTT AGC TAC CTC TGT GAC CTT GCC CCT GAA                    810
Val Ser Tyr Leu Cys Asp Leu Ala Pro Glu
            695                 700

GCC CCT CCT CCT ACT CTG CCC CCC CAC ATG                    840
Ala Pro Pro Pro Thr Leu Pro Pro His Met
            705                 710

GCA CAA GTC ACT GTG GGC CCG GGG CTC TTG                    870
Ala Gln Val Thr Val Gly Pro Gly Leu Leu
            715                 720

GGG GTT TCG ACC CTG GGG CCC AAG AGG AAC                    900
Gly Val Ser Thr Leu Gly Pro Lys Arg Asn
            725                 730

TCC ATG GTT CTG GAT GTG GCG TTC GTC CTG                    930
Ser Met Val Leu Asp Val Ala Phe Val Leu
            735                 740

GAA GGA TCG GAC AAA ATT GGT GAA GCC GAC                    960
Glu Gly Ser Asp Lys Ile Gly Glu Ala Asp
            745                 750

(2) INFORMATION FOR SEQ ID NO: 2:

(i) SEQUENCE CHARACTERISTICS:
        (A) LENGTH: 26
        (B) TYPE: Nucleic acid
        (C) STRANDEDNESS: single stranded
        (D) TOPOLOGY: Linear (xi) SEQUENCE DESCRIPTION: SEQ ID NO: 2:

ACGAATTC CGG CGT TTT GCC TCA GGA                           26

(2) INFORMATION FOR SEQ ID NO: 3:

(i) SEQUENCE CHARACTERISTICS:
        (A) LENGTH: 35 base pairs
        (B) TYPE: Nucleic acid
        (C) STRANDEDNESS: single stranded
        (D) TOPOLOGY: Linear (xi) SEQUENCE DESCRIPTION: SEQ ID NO: 3:

GAAGCT TAC CAT GGA GTT CCT CTT GGG CCC CAG GG              35

(2) INFORMATION FOR SEQ ID NO: 4:

(i) SEQUENCE CHARACTERISTICS:
        (A) LENGTH: 36 base pairs
        (B) TYPE: Nucleic acid
        (C) STRANDEDNESS: single stranded
        (D) TOPOLOGY: Linear (xi) SEQUENCE DESCRIPTION: SEQ ID NO: 4:

GAC AAC ATC AAC GTG GCC AAT CTG GCC GTG CTC AGG            36

(2) INFORMATION FOR SEQ ID NO: 5:

(i) SEQUENCE CHARACTERISTICS:
        (A) LENGTH: 30 base pairs
        (B) TYPE: Nucleic acid
        (C) STRANDEDNESS: single stranded
        (D) TOPOLOGY: Linear (xi) SEQUENCE DESCRIPTION: SEQ ID NO: 5:

CGG CTC CTG GCC GGC TTC ACC GGT GAG GTT                    30
```

(2) INFORMATION FOR SEQ ID NO: 6:

(i) SEQUENCE CHARACTERISTICS:
        (A) LENGTH: 19 base pairs
        (B) TYPE: Nucleic acid
        (C) STRANDEDNESS: single stranded
        (D) TOPOLOGY: Linear (xi) SEQUENCE DESCRIPTION: SEQ ID NO: 6:

```
G CCT GCT GCC GTA GAA ATC                                          19
```

(2) INFORMATION FOR SEQ ID NO: 7:

(i) SEQUENCE CHARACTERISTICS:
        (A) LENGTH: 21 base pairs
        (B) TYPE: Nucleic acid
        (C) STRANDEDNESS: single stranded
        (D) TOPOLOGY: Linear (xi) SEQUENCE DESCRIPTION: SEQ ID NO: 7:

```
GGC AAG GTC ACC GAG GTA GCT                                        21
```

(2) INFORMATION FOR SEQ ID NO: 8:

(i) SEQUENCE CHARACTERISTICS:
        (A) LENGTH: 36
        (B) TYPE: Nucleic acid
        (C) STRANDEDNESS: single stranded
        (D) TOPOLOGY: Linear (xi) SEQUENCE DESCRIPTION: SEQ ID NO: 8:

```
GAC AAC ATC ACC GTG GCC                                            18
AAT CTG GCC GTG CTC AGG                                            36
```

(2) INFORMATION FOR SEQ ID NO: 9:

(i) SEQUENCE CHARACTERISTICS:
        (A) LENGTH: 36
        (B) TYPE: Nucleic acid
        (C) STRANDEDNESS: single stranded
        (D) TOPOLOGY: Linear (xi) SEQUENCE DESCRIPTION: SEQ ID NO: 9:

```
GAC AAC ATC ACC GTG GCC AAT CTG GCC GTG CTC AGG                    36
```

(2) INFORMATION FOR SEQ ID NO: 10:

(i) SEQUENCE CHARACTERISTICS:
        (A) LENGTH: 30 base pairs
        (B) TYPE: Nucleic acid
        (C) STRANDEDNESS: single stranded
        (D) TOPOLOGY: Linear (xi) SEQUENCE DESCRIPTION: SEQ ID NO: 10:

```
GAC TTG TGC CAT GTC GTA GCT AAC GAT CTC                            30
```

(2) INFORMATION FOR SEQ ID NO: 11:

(i) SEQUENCE CHARACTERISTICS:
        (A) LENGTH: 21
        (B) TYPE: Amino acid
        (C) STRANDEDNESS:
        (D) TOPOLOGY: Linear (xi) SEQUENCE DESCRIPTION: SEQ ID NO: 11:

```
Met Ala Ser Met Thr Gly Gly Gln Gln Met
                 5                  10

Gly Arg Gly Ser Pro Gly Leu Gln Glu Phe Arg
```

```
                        15                  20

(2) INFORMATION FOR SEQ ID NO: 12:

(i) SEQUENCE CHARACTERISTICS:
        (A) LENGTH: 24 base pairs
        (B) TYPE: Nucleic acid
        (C) STRANDEDNESS: single stranded
        (D) TOPOLOGY: Linear (xi) SEQUENCE DESCRIPTION: SEQ ID NO: 12:

GAA GGA GAT ATA CAT ATG GCT AGC                                 24

(2) INFORMATION FOR SEQ ID NO: 13:

(i) SEQUENCE CHARACTERISTICS:
        (A) LENGTH: 30 base pairs
        (B) TYPE: Nucleic acid
        (C) STRANDEDNESS: single stranded
        (D) TOPOLOGY: Linear (xi) SEQUENCE DESCRIPTION: SEQ ID NO: 13:

GCC TCC CGG CTC CTG CAT ATG TAT ATC TCC                         30

(2) INFORMATION FOR SEQ ID NO: 14:

(i) SEQUENCE CHARACTERISTICS:
        (A) LENGTH: 23
        (B) TYPE: Amino acid
        (C) STRANDEDNESS:
        (D) TOPOLOGY: Linear (xi) SEQUENCE DESCRIPTION: SEQ ID NO: 14:

Val Ser Ser Asp Pro Ala Ala Asn Lys Ala
                 5                  10

Arg Lys Glu Ala Glu Leu Ala Ala Ala Thr
                15                  20

Ala Glu Gln (2) INFORMATION FOR SEQ ID NO: 15:

(i) SEQUENCE CHARACTERISTICS:
        (A) LENGTH: 320
        (B) TYPE: Amino acid
        (C) STRANDEDNESS:
        (D) TOPOLOGY: Linear (xi) SEQUENCE DESCRIPTION: SEQ ID NO: 15:

Glu Asp Cys Pro Val Cys Glu Val Ala Gly
                435                 440

Arg Arg Phe Ala Ser Gly Lys Lys Val Thr
                445                 450

Leu Asn Pro Ser Asp Pro Glu His Cys Gln
                455                 460

Ile Cys His Cys Asp Val Val Asn Leu Thr
                465                 470

Cys Glu Ala Cys Gln Glu Pro Gly Gly Leu
                475                 480

Val Val Pro Pro Thr Asp Ala Pro Val Ser
                485                 490

Pro Thr Thr Leu Tyr Val Glu Asp Ile Ser
                495                 500

Glu Pro Pro Leu His Asp Phe Tyr Cys Ser
```

```
                        505                 510
Arg Leu Leu Asp Leu Val Phe Leu Leu Asp
                515                 520

Gly Ser Ser Arg Leu Ser Glu Ala Glu Phe
                525                 530

Glu Val Leu Lys Ala Phe Val Val Asp Met
                535                 540

Met Glu Arg Leu Arg Ile Ser Gln Lys Trp
                545                 550

Val Arg Val Ala Val Glu Tyr His Asp
                555                 560

Gly Ser His Ala Tyr Ile Gly Leu Lys Asp
                565                 570

Arg Lys Arg Pro Ser Glu Leu Arg Arg Ile
                575                 580

Ala Ser Gln Val Lys Tyr Ala Gly Ser Gln
                585                 590

Val Ala Ser Thr Ser Glu Val Leu Lys Tyr
                595                 600

Thr Leu Phe Gln Ile Phe Ser Lys Ile Asp
                605                 610

Arg Pro Glu Ala Ser Arg Ile Ala Leu Leu
                615                 620

Leu Met Ala Ser Gln Glu Pro Gln Arg Met
                625                 630

Ser Arg Asn Phe Val Arg Tyr Val Gln Gly
                635                 640

Leu Lys Lys Lys Val Ile Val Ile Pro
                645                 650

Val Gly Ile Gly Pro His Ala Asn Leu Lys
                655                 660

Gln Ile Arg Leu Ile Glu Lys Gln Ala Pro
                665                 670

Glu Asn Lys Ala Phe Val Leu Ser Ser Val
                675                 680

Asp Glu Leu Glu Gln Gln Arg Asp Glu Ile
                685                 690

Val Ser Tyr Leu Cys Asp Leu Ala Pro Glu
                695                 700

Ala Pro Pro Pro Thr Leu Pro Pro His Met
                705                 710

Ala Gln Val Thr Val Gly Pro Gly Leu Leu
                715                 720

Gly Val Ser Thr Leu Gly Pro Lys Arg Asn
                725                 730

Ser Met Val Leu Asp Val Ala Phe Val Leu
                735                 740

Glu Gly Ser Asp Lys Ile Gly Glu Ala Asp
                745                 750
```

THERAPEUTIC DOMAINS OF VAN WILLEBRAND FACTOR

CROSS-REFERENCE TO RELATED APPLICATIONS

This is a continuation-in-part of application Ser. No. PCT/US91/07756, filed in the United States Receiving Office on Oct. 17, 1991, which designates the United States and is a continuation-in-part of U.S. application Ser. Nos. 07/613,004, filed Nov. 13, 1990 now abandoned, and 07/600,183, filed Oct. 17, 1990, now abandoned, said application Ser. No. 07/613,004 being a continuation-in-part of said application Ser. No. 07/600,183, which is itself a continuation-in-part of U.S. application Ser. No. 07/519,606, filed May 7, 1990, now U.S. Pat. No. 5,238,919, which is continuation-in-part of U.S. application Ser. No. 07/270,488, filed Nov. 4, 1988, now abandoned, which is a continuation of U.S. application Ser. No. 06/869,188, filed May 30, 1986, and now abandoned.

This invention was made with government support under HL 15491 and HL 42846, awarded by the National Institutes of Health. The government has certain rights in the invention.

FIELD OF THE INVENTION

This invention relates to polypeptides which are useful in the treatment of vascular disorders such as thrombosis. This invention further relates to the production by recombinant DNA-directed methods of pharmacologically useful quantities of the polypeptides of the present invention.

The term "hemostasis" refers to those processes which comprise the defense mechanisms of the body against loss of circulating blood caused by vascular injury. Processes which are normal as a physiologic response to vascular injury may lead in pathologic circumstances, such as in a patient afflicted with atherosclerotic vascular disease or chronic congestive heart failure, to the formation of undesired thrombi (clots) with resultant vascular occlusion. Impairment of blood flow to organs under such circumstances may lead to severe pathologic states, including myocardial infarction, a leading cause of mortality in developed countries.

The restriction or termination of the flow of blood within the circulatory system in response to a wound or as a result of a vascular disease state involves a complex series of reactions which can be divided into two processes, primary and secondary hemostasis. Primary hemostasis refers to the process of platelet plug or soft clot formation. The platelets are non-nucleated discoid structures approximately 2–5 microns in diameter derived from megakaryocytic cells. Effective primary hemostasis is accomplished by platelet adhesion, the interaction of platelets with the surface of damaged vascular endothelium on which are exposed underlying collagen fibers and/or other adhesive macromolecules such as proteoglycans and glycosaminoglycans to which platelets bind.

Secondary hemostasis involves the reinforcement or crosslinking of the soft platelet clot. This secondary process is initiated by proteins circulating in the plasma (coagulation factors) which are activated during primary hemostasis, either in response to a wound or a vascular disease state. The activation of these factors results ultimately in the production of a polymeric matrix of the protein fibrinogen (then called fibrin) which reinforces the soft clot.

The present invention relates to antiplatelet drugs. Antiplatelet drugs include drugs which suppress primary hemostasis by altering platelets or their interaction with other circulatory system components.

REPORTED DEVELOPMENTS

Specific antiplatelet drugs operate by one or several mechanisms. A first example involves reducing the availability of ionized calcium within the platelet cytoplasm thereby impairing activation of the platelet and resultant aggregation. Pharmaceuticals representative of this strategy include prostacyclin, and also Persatine® (dipyridamole) which may affect calcium concentrations by affecting the concentration of cyclic AMP. Numerous side effects related to the administration of these compounds have been reported. An additional class of antiplatelet drugs acts by inhibiting the synthesis of thromboxane $A_2$ within the platelet, reducing the platelet activation response. Non-steroidal anti-inflammatory agents, such as ibuprofen, phenolbutazone and napthroxane may produce a similar effect by competitive inhibition of a particular cyclooxygenase enzyme, which catalyzes the synthesis of a precursor of thromboxane $A_2$. A similar therapeutic effect may be derived through the administration of aspirin which has been demonstrated to irreversably acetylate a cyclooxygenase enzyme necessary to generate thromboxane $A_2$. A third antiplatelet mechanism has involved the platelet membrane so as to interfere with surface receptor function. One such drug is dextran, a large branched polysaccharide, which is believed to impair the interaction of fibrinogen with platelet receptors that are exposed during aggregation. Dextran is contraindicated for patients with a history of renal problems or with cardiac impairment. The therapeutic ticlopidine is stated to inhibit platelet adhesion and aggregation by suppressing the binding of von Willebrand factor and/or fibrinogen to their respective receptors on the platelet surface. However, it has been found that ticlopidene possesses insufficient specificity to eliminate the necessity of administering large doses which, in turn, may be associated with clinical side effects.

The aforementioned pharmaceuticals are foreign to the body and may cause numerous adverse clinical side effects, there being no way to prevent such compounds from participating in other aspects of a patient's physiology or biochemistry, particularly if high doses are required. It would be desirable to provide for pharmaceuticals having such specificity for certain of the reactions of hemostasis, that they could be administered to patients at low doses, such doses being much less likely to produce adverse effects in patients.

An example of a pharmaceutical which is representative of a therapeutic that is derived from natural components of the hemostatic process is described in EPO Publication No. 317278. This publication discloses a method for inhibiting thrombosis in a patient by administering to the patient a therapeutic polypeptide comprised of the aminoterminal region of the a chain of platelet membrane glycoprotein Ib, or a subfragment thereof.

The present invention is directed to the provision of antithrombotic polypeptides derived from von Willebrand factor, one of the proteins of the hemostatic mechanism.

SUMMARY OF THE PRESENT INVENTION

In accordance with the present invention, there is provided a polypeptide which is capable of inhibiting binding of von Willebrand factor (vWF) to platelets and which is selected from the group consisting of:

(A) a polypeptide comprising a domain, hereinafter the "(A) domain", consisting essentially of an amino acid sequence that corresponds to the amino acid sequence of that fragment of mature von Willebrand factor subunit having its amino terminus at about $Cys^{509}$ and its carboxy terminus at about $Cys^{695}$;

(B) a polypeptide comprising said (A) domain and covalently linked thereto a "second domain" consisting essentially of an amino acid sequence that corresponds to the amino acid sequence of that fragment of mature vWF subunit having its amino terminus at about $Arg^{441}$ and its carboxy terminus at about $Tyr^{508}$, or a subfragment or combination of subfragments thereof, wherein said domains are linked by a covalent bond between the carboxy terminus of said second domain and the amino terminus of said (A) domain; and (C) a polypeptide comprising said (A) domain and covalently linked thereto another domain, hereinafter "other domain", consisting essentially of an amino acid sequence that corresponds to the amino acid sequence of that fragment of mature vWF subunit having its amino terminus at about $Asp^{696}$ and its carboxy terminus at about $Val^{733}$, or a subfragment or combination of subfragments thereof, wherein said domains are linked by a covalent bond between the carboxy terminus of said (A) domain and the amino terminus of said other domain.

Representative polypeptides of the invention are:

(A) a polypeptide having an amino terminus at about $Tyr^{508}$ and a carboxy terminus at about $Asp^{696}$; and (B) a polypeptide having an amino terminus at about $Tyr^{508}$ and a carboxy terminus at about $Pro^{704}$.

A preferred method for providing the polypeptides of the invention comprises:

(A) providing an encoding DNA sequence; and (B) inserting the DNA sequence into a suitable vector to create a construct comprising an expression plasmid or viral expression vector, which construct is capable of directing the expression in a host cell of said polypeptide; and (C) transforming a host cell with said expression plasmid or viral expression vector; and (D) culturing said transformed host cell under conditions that cause expression within the host cell of the polypeptide.

Another aspect of the present invention is the provision of a therapeutic composition which comprises a therapeutically effective amount of one or more polypeptides of the present invention and a pharmaceutically acceptable carrier.

Still another aspect of the invention provides a method of inhibiting or treating thrombosis in a patient which comprises administering to the patient an effective amount of one or more of the therapeutic compositions of the invention.

BRIEF DESCRIPTION OF THE DRAWINGS

FIGS. 1A and 1B show the previously reported amino acid and DNA sequence for the mature von Willebrand factor subunit (human) between residue 431 and residue 750.

FIG. 2 depicts several of the polypeptides of the invention.

DEFINITIONS

Figure 3A:
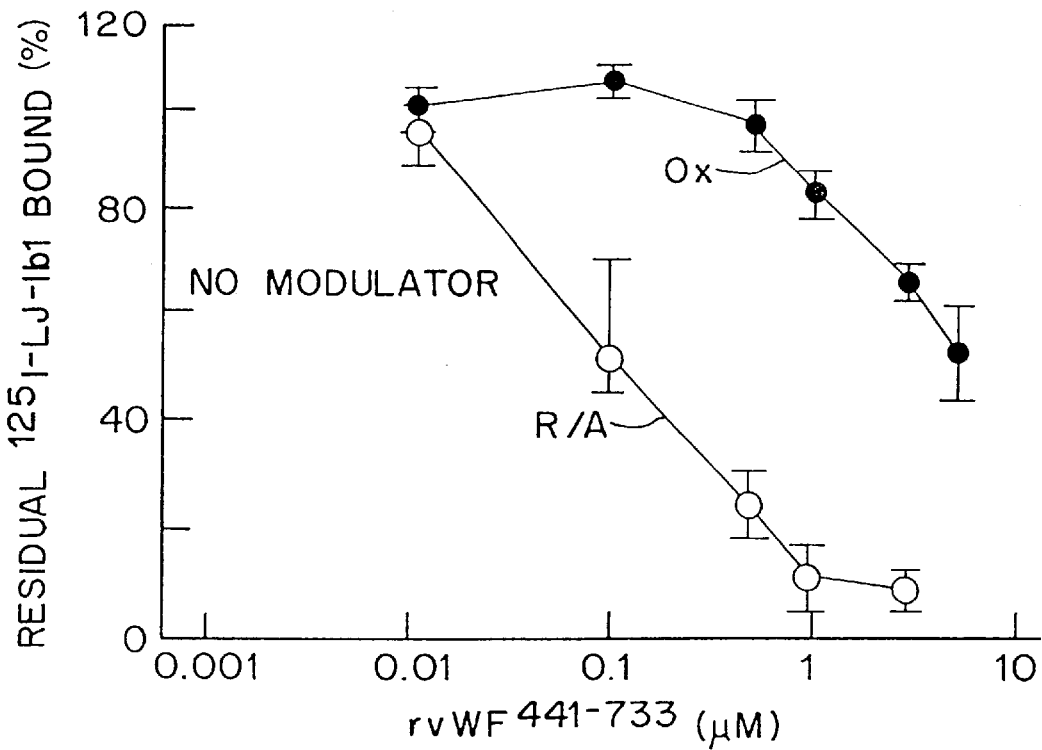
FIGS. 3A and 3B show the relative ability of an oxidized and a reduced form of a vWF-derived polypeptide to inhibit binding to platelets of an antibody directed to GPIbα.

Unless indicated otherwise herein, the following terms have the indicated meanings.

Coding Sequence (Encoding DNA)—DNA sequences which, in the appropriate reading frame, code for the amino acids of a protein. For the purpose of the present invention, it should be understood that the synthesis or use of a coding sequence may necessarily involve synthesis or use of the corresponding complementary strand, as shown by: 5'-CGG·GGA·GGA-3'/3'-GCC·CCT·CCT-5' which "encodes" the tripeptide $NH_2$—arg—gly—gly—$CO_2H$. A discussion of or claim to one strand is deemed to refer to or to claim the other strand and the double stranded counterpart thereof as is appropriate, useful or necessary in the practice of the art.

cDNA—A DNA molecule or sequence which has been enzymatically synthesized from the sequence(s) present in an mRNA template.

Transcribed Strand—The DNA strand whose nucleotide sequence is read 3'→5' by RNA polymerase to produce mRNA. This strand is also referred to as the noncoding strand.

Coding Strand or Non-Transcribed Strand—This strand is the antiparallel compliment of the transcribed strand and has a base sequence identical to that of the mRNA produced from the transcribed strand except that thymine bases are present (instead of uracil bases of the mRNA). It is referred to as "coding" because like mRNA, and when examined 5'→3', the codons for translation may be directly discerned.

Biological Activity—One or more functions, effects of, activities performed or caused by a molecule in a biological context (that is, in an organism or in an in vitro facsimile). A characteristic biological activity of the 52/48 kDa monomeric fragment of the mature von Willebrand factor subunit is the potential ability to bind to only one platelet GPIb receptor thereby enabling the molecule to inhibit botrocetin-induced binding of multimeric vWF to platelets. Other resultant or related effects of the undimerized 52/48 kDa species include inhibition of platelet activation, aggregation, or adhesion to surfaces, and the inhibition of thrombosis.

Reducing Conditions—Refers to the presence of a "reducing" agent in a solution containing von Willebrand factor, or polypeptides derived therefrom, which agent causes the disruption of disulfide bonds of the vWF.

Promoter—DNA sequences upstream from a gene which promote its transcription.

Cloning Vehicle (Vector)—A plasmid, phage DNA or other DNA sequence which is able to replicate in a host cell, typically characterized by one or a small number of endonuclease recognition sites at which such DNA sequences may be cut in a determinable fashion for the insertion of heterologous DNA without attendant loss of an essential biological function of the DNA, e.g., replication, production of coat proteins or loss of expression control regions such as promoters or binding sites, and which may contain a selectable gene marker suitable for use in the identification of host cells transformed therewith, e.g., tetracycline resistance or ampicillin resistance.

Plasmid—A nonchromosomal double-stranded DNA sequence comprising an intact "replicon" such that the plasmid is replicated in a host cell. When the plasmid is placed within a procaryotic or eucaryotic host cell, the characteristics of that cell may be changed (or transformed) as a result of the DNA of the plasmid.

For example, a plasmid carrying the gene for tetracycline resistance ($Tet^R$) transforms a cell previously sensitive to tetracycline into one which is resistant to it. A cell transformed by a plasmid is called a "transformant."

Expression Plasmid—A plasmid into which has been inserted the DNA being cloned, such as the von Willebrand factor structural gene. The DNA sequence inserted therein may also contain sequences which control the translation of mRNA resultant therefrom, and contain restriction endonuclease sites which facilitated assembly of, and may facilitate further modification of, said expression plasmid. An expression plasmid is capable of directing, in a host cell, the expression therein of the encoded polypeptide and usually contains a transcription promoter upstream from the DNA sequence of the encoded structural gene. An expression plasmid may or may not become integrated into the host chromosomal DNA. For the purpose of this invention, an integrated plasmid is nonetheless referred to as an expression plasmid.

Viral Expression Vector—A viral expression vector is similar to an expression plasmid except that the DNA may be packaged into a viral particle that can transfect cells through a natural biological process.

Downstream—A nucleotide of the transcribed strand of a structural gene is said to be downstream from another section of the gene if the nucleotide is normally read by RNA polymerase after the earlier section of the gene. The complimentary nucleotide of the nontranscribed strand, or the corresponding base pair within the double stranded form of the DNA, are also denominated downstream.

Additionally, and making reference to the direction of transcription and of translation within the structural gene, a restriction endonuclease sequence added upstream (or 5') to the gene means it is added before the sequence encoding the amino terminal end of the protein, while a modification created downstream (or 3') to the structural gene means that it is beyond the carboxy terminus-encoding region thereof.

von Willebrand factor (vWF)—It is understood that all references herein to von Willebrand factor refer to vWF in humans. The term "von Willebrand factor" is intended to include within its scope any and all of the terms which are defined directly below.

Additionally, von Willebrand factor is found as a component of the subendothelial matrix, as a component of the α-granules secreted by activated platelets, and as a circulating blood plasma protein. It is possible that the three-dimensional subunit structure or multisubunit structure of vWF varies in these different contexts potentially caused, for example, by differences in glycosylation. Such differences do not prevent useful therapeutic vWF-derived polypeptides from being produced from the vWF DNA sequences of endothelial cells or megakaryocytes according to the practice of this invention.

Furthermore it is possible that there are minor biologically unimportant differences between the actual DNAs and polypeptides manipulated or otherwise utilized in the practice of the invention and the structural sequences of amino acids or nucleotides thereof as reported herein. It is understood that the invention encompasses any such biologically unimportant variations.

Pre-pro-vWF—von Willebrand factor is subject to extensive posttranslational processing. "Pre-pro-vWF" contains (from the N to the C terminus) a signal peptide comprised of approximately 22 amino acid residues, a propeptide of approximately 741 amino acids, and then the approximate 2,050 residues of circulating vWF.

Pro-vWF—The signal peptide has been removed from pre-pro-vWF.

Mature vWF—Circulating vWF as found in the plasma or as bound to the subendothelium. It consists of a population of polypeptide monomers which are typically associated into numerous species of multimers thereof, each subunit of which being 2,050 residues in length. Additionally, when expressed in mammalian cells, mature vWF is usually glycosylated.

Signal Peptide (Sequence)—A signal peptide is the sequence of amino acids in a newly translated polypeptide which signals translocation of the polypeptide across the membrane of the endoplasmic reticulum and into the secretory pathway of the cell. A signal peptide typically occurs at the beginning (amino terminus) of the protein and is 20–40 amino acids long with a stretch of approximately 5–15 hydrophobic amino acids in its center. Typically the signal sequence is proteolytically cleaved from the protein during, or soon after, the process of translocation into the endoplasmic reticulum. That portion of a gene or cDNA encoding a signal peptide may also be referred to as a signal sequence.

Table 1 shows the standard three letter designations for amino acids as used in the application.

TABLE I

| Alanine | Ala |
|---|---|
| Cysteine | Cys |
| Aspartic Acid | Asp |
| Glutamic Acid | Glu |
| Phenylalanine | Phe |
| Glycine | Gly |
| Histidine | His |
| Isoleucine | Ile |
| Lysine | Lys |
| Leucine | Leu |
| Methionine | Met |
| Asparagine | Asn |
| Proline | Pro |
| Glutamine | Gln |
| Arginine | Arg |
| Serine | Ser |
| Threonine | Thr |
| Valine | Val |
| Tryptophan | Trp |
| Tyrosine | Tyr |

DETAILED DESCRIPTION OF THE INVENTION

A "Sequence Listing" pursuant to 37 CFR §1.821(c) for nucleotide and amino acid sequences disclosed or referred to herein is appended and made part of this application.

The terms "peptide" and "polypeptide" are used herein interchangeably.

As set forth above, the antithrombotic polypeptides of the present invention are based upon fragments of the natural occurring protein von Willebrand factor (hereinafter "vWF"). For background purposes, there is set forth hereafter information concerning this protein and its role in hemostasis and thrombosis.

Description of the Role of vWF in Hemostasis and Thrombosis vWF performs an essential role in normal hemostasis during vascular injury and is also of central importance in the pathogenesis of acute thrombotic occlusions in diseased blood vessels. Both of these roles involve the interaction of vWF with platelets which are induced to bind at the affected site and are then crosslinked. It is believed that single platelets first adhere to a thrombogenic surface after which they become activated, a process involving major metabolic changes and significant morphological changes within the platelet. Activation is evidenced by the discharge of platelet storage granules containing adhesive substances such as von Willebrand factor (an adhesive protein), and the expression on the surface of the platelet of additional functional adhesive sites. Once activated, and as a part of normal hemostasis, platelet cells become aggregated, a process which involves extensive crosslinking of the platelet cells with additional types of adhesive proteins.

As stated above, these processes are normal as a physiologic response to vascular injury. However, they may lead in pathologic circumstances, such as in diseased vessels, to formation of undesired platelet thrombi with resultant vascular occlusion.

Other circumstances in which it is desirable to prevent deposition of platelets in blood vessels include the prevention and treatment of stroke, and to prevent occlusion of arterial grafts. Platelet thrombus formation during surgical procedures may also interfere with attempts to relieve pre-existing vessel obstructions.

The adhesion of platelets to damaged or diseased vessels occurs through mechanisms that involve specific platelet membrane receptors which interact with specialized adhesive molecules. One such platelet receptor is the glycoprotein Ib-IX complex which consists of a noncovalent association of two integral membrane proteins, glycoprotein Ib (GPIb) and glycoprotein IX (GPIX). The adhesive ligand of the GPIb-IX complex is the protein von Willebrand factor which is found as a component of the subendothelial matrix, as a component of the α-granules secreted by activated platelets, and also as a circulating blood plasma protein. The actual binding site of the vWF to the GPIb-IX receptor has been localized on the amino terminal region of the a chain of glycoprotein Ib. The full-length α chain is also referred to as "GPIb(α)".

It is believed that the interaction of multimeric vWF with glycoprotein Ib-IX complex (at GPIb(α)) results in platelet activation and facilitates the recruitment of additional platelets to a now growing thrombus. The rapidly accumulating platelets are also crosslinked (aggregated) by the binding of fibrinogen at platelet glycoprotein IIb-IIIa receptor sites, and possibly also by vWF at these sites, and/or at additional glycoprotein Ib-IX receptor sites. In addition, the glycoprotein IIb/IIIa receptor may also be involved in the formation of the initial monolayer of platelets. Of particular importance in this process is the multimeric and multivalent character of circulating vWF, which enables the macromolecule to effectively carry out its binding and bridging functions.

Inactivation of the GPIbα receptors on the platelets of a patient thereby inhibiting the binding and bridging ability of vWF, would be of great medical importance for treating or inhibiting thrombosis. Accordingly, the present invention relates to the development of polypeptides which are effective in accomplishing the foregoing.

Information Concerning the Structure of vWF and the Design of Therapeutics Derived Therefrom The domain of the von Willebrand factor subunit which binds to the platelet membrane glycoprotein Ib-IX receptor (GPIb(α)) has been identified within a fragment of vWF. The fragment may be generated by trypsin digestion, followed by disulfide reduction, and extends from approximately residue 449 (valine) of the circulating subunit to approximately residue 728 (lysine) thereof. Current evidence indicates that this segment also contains (between residues 509 and 695 thereof) binding domains for components of the subendothelium, such as collagen and proteoglycans, although other regions of the mature vWF subunit may be more important in recognizing these substances (an additional proteoglycan or heparin binding site is located in residues 1–272 of the mature subunit and an additional collagen binding site within residues 910–1110 thereof).

FIGS. 1A and 1B (SEQ ID NO: 1, see also SEQ ID NO: 15) shows the previously reported amino acid and DNA sequence for the mature von Willebrand factor subunit (human) between residue 431 and residue 750. The 52/48 kDa fragment produced by tryptic digestion has an amino terminus at residue 449 (valine) and extends approximately to residue 728 (lysine). Amino acids are shown by standard three letter designations. The DNA sequence is represented by the coding strand (nontranscribed strand). Very little polymorphism has been reported in the 52/48 human sequence with one significant exception—histidine/aspartic acid at position 709, see Mancuso, D.J. et al. *J. Biol. Chem.*, 264(33), 19514–19527, Table V, (1989). DNA sequences used for the experiments described in the Example section below contain an aspartic acid codon for residue 709 (codon GAC), although placement of histidine at residue position 709 (the other known naturally occurring amino acid at this position in the human sequence, codon CAC) is also useful in the practice of the invention.

With respect to the therapeutic antithrombotic polypeptides of the present invention, the following information concerning vWF is of particular interest.

A fragment of mature von Willebrand factor having platelet glycoprotein Ib(α) binding activity and of approximately 116,000 (116 kDa) molecular weight is isolated by digesting vWF with trypsin. If the 116 kDa fragment is treated with a reducing agent capable of cleaving disulfide bonds, a pair of identical fragments is generated. Each of the identical fragments (which together comprise the 116 kDa polypeptide) has an apparent molecular weight of about 52,000 (52 kDa). (Polypeptide molecular weight are typically measured by migration, relative to standards, in a denaturing gel electrophoresis system. Weight values which result are only approximate.)

Typically, the 52,000 molecular weight fragment is referred to as a "52/48" fragment reflecting the fact that human enzyme systems glycosylate the fragment contributing to its molecular weight. The amount of glycosylation varies from molecule to molecule, with two weights, 52,000 and 48,000, being most common.

The 52/48 fragment has been demonstrated to have as its amino-terminus residue 449 (valine) of the mature subunit, and as its carboxy-terminus residue 728 (lysine) thereof. Without the additional weight contributed by glycosylation, such as, for example, if a comparable fragment were expressed from a recombinant bacterial cell, the polypeptide would have a molecular weight of approximately 38,000.

The 52/48 fragment has been demonstrated to competitively inhibit the binding of von Willebrand factor to platelets. However, manipulation of the 52/48 fragment or its unglycosylated 38 kDa equivalent has proved difficult. Successful manipulation of the fragment has typically required that the cysteine residues thereof be reduced and permanently alkylated. Without this treatment, undesired reaction of the cysteine residues thereof invariably occurs, leading to the formation of insoluble and biologically inactive polypeptide aggregates unsuited for effective use as therapeutics.

It is known that the residue 449–728 fragment of mature von Willebrand factor subunit, which contains the platelet glycoprotein Ib(α) binding domain, has cysteine residues at positions 459, 462, 464, 471, 474, 509 and 695. It is known also that all of the cysteine residues of the mature vWF subunit are involved in disulfide bonds. (Legaz, et al., *J. Biol. Chem.*, 248, 3946–3955 (1973)).

Marti, T. et al. *Biochemistry*, 26, 8099–8109 (1987) conclusively identified mature subunit residues 471 and 474 as being involved in an intrachain disulfide bond. Residues 509 and 695 were identified as being involved in a disulfide bond, although it was not demonstrated whether this pairing was intrachain or interchain (that is, within the same mature vWF subunit).

Mohri, H. et al. *J. Biol. Chem.*, 263(34), 17901–17904 (1988) inhibited the ristocetin-induced binding of $^{125}$I-labelled multimeric vWF to formalin-fixed platelets with peptide subfragments of the 449–728 subunit fragment. Peptide subfragments fifteen residues in length were synthesized and tested. Those peptides which represent subunit sequence contained within, or overlapping with, two distinct regions, Leu$^{469}$ to Asp$^{498}$ and Glu$^{689}$ to Val$^{713}$ were found to be active.

Mohri concluded that the GPIb($\alpha$) binding domain of vWF was formed by residues contained in two discontinuous sequences Cys$^{474}$-Pro$^{488}$ and Leu$^{694}$-Pro$^{708}$ maintained in proper conformation in native vWF by disulfide bonding, although the authors were unable to identify the cysteine residue which formed the stabilizing bond(s) and whether the bonds were intra or interchain.

The present invention provides for polypeptides derived from the residue 449–728 region of the mature von Willebrand factor subunit which are useful in the treatment of vascular disorders such as thrombosis.

Such molecules can be made most efficiently from DNA which encodes that fragment of mature von Willebrand factor subunit comprising essentially the amino acid sequence from approximately residue 441 (arginine) to approximately residue 733 (valine), or which encodes any subset of said amino acid sequence, or a mutant polypeptide fragment, or subset thereof, which contains fewer cysteine residues than that of the comparable wild-type amino acid sequence. A preferred method for the preparation of the molecules comprises culturing a host organism transformed with a biologically functional expression plasmid which contains a mutant DNA sequence encoding a portion of said von Willebrand factor subunit under conditions which effect expression of the mutant von Willebrand factor fragment, or a subset thereof, by the host organism and recovering said fragment therefrom.

A preferred means for effecting mutagenesis of cysteine codons in a vWF DNA to codons encoding amino acids incapable of disulfide bonding is based upon the site directed mutagenesis procedure of Kunkel, T.A., *Proc. Natl. Acad. Sci. U.S.A.*, 82, 488–492 (1985). Such mutant DNA sequences may then be expressed from either recombinant-bacterial or recombinant-eucaryotic host cell systems.

First Embodiment of the Invention

An important aspect of this embodiment of the invention is the provision of compositions of said vWF-derived polypeptides which are less prone to aggregation and denaturation caused by undesired disulfide bonding within the inclusion bodies of host expression cells (or resultant from inclusion body solubilization procedures) than previous preparations. The development employs mutagenesis to limit the number of cysteine residues present within said polypeptides.

Mutagenesis of vWF DNA Encoding The Mature Subunit Residue 449–728 Region

A variety of molecular biological techniques are available which can be used to change cysteine codons for those of other amino acids. Suitable techniques include mutagenesis using a polymerase chain reaction, gapped-duplex mutagenesis, and differential hybridization of an oligonucleotide to DNA molecules differing at a single nucleotide position. For a review of suitable codon altering techniques, see Kraik, C. "Use of Oligonucleotides for Site Specific Mutagenesis", *Biotechniques*, Jan/Feb 1985 at page 12.

In the practice of this embodiment, it preferred to use the site-directed or site-specific mutagenesis procedure of Kunkel, T.A., *Proc. Natl. Acad. Sci. USA*, 82, 488–492 (1985). This procedure takes advantage of a series of steps which first produces, and then selects against, a uracil-containing DNA template. Example 1 of the present invention explains in detail the mutagenesis techniques used to create mutant vWF cDNA.

Other publications which disclose site-directed mutagenesis procedures are: Giese, N.A. et al., *Science*, 236, 1315 (1987); U.S. Pat. No. 4,518,584; and U.S. Pat. No. 4,959,314.

It is also preferred in the practice of this embodiment to cause to be substituted for one or more of the cysteine codons of the wild type DNA sequence codons for one or more of the following amino acids: alanine, threonine, serine, glycine, and asparagine. Replacement with alanine and glycine codons is most preferred. The selection of a replacement for any particular codon is generally independent of the selection of a suitable replacement at any other position.

The following are representative examples of the types of codon substitutions which can be made, using as an example cysteine residue 459:

(A) the codon for cysteine 459 could be replaced by a codon for glycine; or (B) the codon for cysteine 459 could be replaced by two or more codons such as one for serine and one for glycine, such replacement resulting in a new amino acid sequence: -His$^{458}$-Ser$^{459(a)}$-Gly$^{459(b)}$-Gln$^{460}$-; or (C) the codon for cysteine 459 could be deleted from the cDNA, such deletion resulting in a shortened amino acid sequence represented by: -His$^{458}$-Gln$^{460}$-; or (D) one or more codons for residues adjacent to cysteine residue 459 could be deleted along with codon 459 as represented by: -Glu$^{457}$Gln-$^{460}$-.

It is contemplated that codons for amino acids other than alanine, threonine, serine, glycine or asparagine will also be useful in the practice of the invention depending on the particular primary, secondary, tertiary and quaternary environment of the target cysteine residue.

It is considered desirable in the practice of this embodiment to provide as a replacement for any particular cysteine residue of the 449–728 tryptic vWF subunit fragment an amino acid which can be accommodated at the cysteine position with minimal perturbation of the secondary structure (such as $\alpha$-helical or $\beta$-sheet) of the wild type amino acid sequence subsegment within which the cysteine position is located. In the practice of the present invention, alanine, threonine, serine, glycine and asparagine will generally be satisfactory because they are, like cysteine, neutrally charged and have side chains which are small or relatively small in size.

Substantial research has been conducted on the subject of predicting within which types of structural domains of proteins ($\alpha$-helix, $\beta$-sheet, or random coil) one is most likely to find particular species of amino acids. Serine is a preferred amino acid for use in the practice of this invention because it most closely approximates the size and polarity of cysteine and is believed not to disrupt $\alpha$-helical and $\beta$-sheet domains.

Reference, for example, to Chou, P.Y. et al., *Biochemistry*, 13(2), 211–222 (1974) and Chou, P.Y. et al., "Prediction of Protein Conformation," *Biochemistry*, 13(2), 222–244 (1974) provides further information useful in the selection of replacement amino acids. Chou, P.Y. et al. predicted the secondary structure of specified polypeptide sequence segments based on rules for determining which species of amino acids therein are likely to be found in the center of, for example, an alpha helical region, and which residues thereof would be likely to terminate propagation of a helical zone, thus becoming a boundary residues or helix breakers. According to Chou, P.Y. et al., supra, at 223, cysteine and the group of threonine, serine, and asparagine are found to be indifferent to α-helical structure, as opposed to being breakers or formers of such regions. Thus, threonine, serine and asparagine are likely to leave unperturbed an α-helical region in which a potential target cysteine might be located. Similarly, glycine, alanine and serine were found to be more or less indifferent to the formation of β-regions. It is noted that serine, threonine and asparagine residues represent possible new sites of glycosylation making them potentially unsuitable replacement residues at certain positions in secretory proteins subject to glycosylation.

Generally, the primary consideration which should be taken into account in connection with selecting suitable amino acid replacements is whether the contemplated substitution will have an adverse effect on the tertiary structure of the fragment. Thus, other amino acids may be suitable as acceptable substitutes for particular cysteine residues as long as the new residues do not introduce undesired changes in the tertiary structure of the 449–728 fragment. Reactivity with NMC-4 antibody is recommended as a test of whether a mutant polypeptide has the desired therapeutic properties.

Particularly preferred mutant polypeptides of the present invention are patterned upon a monomeric form of the residue 449–728 domain of the mature subunit fragment, as opposed to a dimer thereof which could provide a bridging function between two platelets. Normally, those codons in a vWF DNA fragment for specific cysteines which normally participate in interchain disulfide bonding should be replaced. Cysteine codons encoding residues which form intrachain disulfide bonds should be left unmutated, if the intrachain bond is demonstrated to confer upon the subunit fragment important structural features, and if conditions can be found which allow the intrachain bond to form properly.

More specifically, preparation of a mutant polypeptide fragment which corresponds to that fragment of mature von Willebrand subunit having an amino terminus at residue 441 (arginine) and a carboxy terminus at residue 733 (valine), but which differs therefrom in that each of the cysteine residues thereof is replaced by a glycine residue is disclosed.

The embodiment also teaches that retention of a certain disulfide bond within polypeptides corresponding to the 449–728 vWF subunit region is particularly important for the design of therapeutic molecules derived therefrom. In this regard there is provided a mutant vWF fragment expressed by p5E plasmids, as described in Example 4, and containing an intrachain disulfide bond.

Important factors involved in the design of preferred mutant polypeptides of the invention are described hereafter.

Potential binding sites for collagens and heparinlike glycosaminoglycans exist in the 449–728 tryptic fragment in the loop region between cysteine residues 509 and 695. In the event that binding at these sites impairs the antithrombotic therapeutic utility of the molecule by, for example, also providing bridging to collagen, the polypeptide can be redesigned (for example, by chemical synthesis or proteolysis) to delete all or a portion of the loop region.

von Willebrand factor polypeptides derived from bacterial expression systems substantially lack the glycosylation vWF normally acquires as a result of post-translational processing such as in the Golgi apparatus or Weibel-Palade bodies. The present invention includes within its scope molecules which are made by E.coli BL21(DE3) or other suitable procaryotic host cells and which are enzymatically or chemically glycosylated to more resemble the molecules expressed by mammalian cells.

Alternatively, the DNA encoding sequences can be tranferred to expression plasmids or viral expression vectors capable of causing expresion in mammalian host cells to provide normal glycosylation.

It has been established that both platelets and von Willebrand factor molecules contain large numbers of negative charges such as, for example, those contributed by sialic acid. Such charges can facilitate desirable mutual repulsion of the molecules under non-injury conditions. The addition of one or more positively charged residues of lysine and/or of arginine extending from the amino and/or from the carboxy terminus of the 52/48 tryptic fragment or recombinant equivalents thereof can overcome electrical repulsions with respect to the GPIb-IX receptor facilitating use of the fragment as an antithrombotic therapeutic.

In addition, and with respect to polypeptides patterned upon the 449–728 vWF subunit fragment, it is within the scope of the invention to remove certain cysteine residues by site directed mutagenesis and thereafter inactivating any remaining cysteine residues by chemical inactivation thereof, such as, for example, by S-carboxymethylation.

As described above, successful manipulation of the polypeptides of the invention may require that one or more cysteine residues thereof be altered so that they cannot react with each other causing undesired intrachain or interchain disulfide bonds. In particular, without this treatment, for many of the polypeptides of the invention, undesired reaction of cysteine residues thereof typically occurs leading to the formation of insoluble or biologically inactive polypeptide aggregates unsuited for effective use as therapeutics. Accordingly, many of the polypeptides of the invention are best described as cysteine-altered polypeptides meaning that one or more cysteine residues thereof have been in some way changed to minimize the undesired reactions. It is within the practice of the invention to effect such alteration of said cysteine residues by any of several procedures well known in the art to be effective therefor. Although a preferred form of cysteine alteration comprises mutagenesis of the cysteine codon to that of codons for other amino acids (see Examples 1 and 4) alternate methods are available. One such technique involves treatment of cysteine residues with a reducing agent such as, for example, β-mercaptoethanol or dithiothreitol, "DTT", followed by permanent alkylation (for example, with iodoacetamide). Numerous other covalent labels may be attached to the target cysteine residues to inactivate them, the only requirements being that the label can be supplied under pH conditions which do not irreversibly denature the target polypeptide, said attachment being of a kind which under the conditions to which the fragment is exposed during further processing or storage or use will not allow chemical reaction of the altered cysteine with other cysteine residues.

A mutant polypeptide that is insoluble can be made soluble by covalently linking to it a subdomain of a water soluble polymer, for example, a polyacrylamide. Other techniques can also be used to impart solubility to an otherwise insoluble polypeptide.

In light of the aforementioned, which is generally applicable to all the polypeptides of the invention, there follows hereafter a discussion of means by which mutant polypeptides of the first embodiment of the invention can be prepared.

To accomplish this, a cDNA clone encoding the von Willebrand factor gene (for the pre-propeptide) was utilized.

The cDNA was then subjected to enzymatic amplification in a polymerase chain reaction using oligonucleotides which flanked the indicated region. The first oligonucleotide representing coding strand DNA contained an EcoRI site 5' to the codon for residue 441 (arginine) and extended to the codon for residue 446 (glycine). The second oligonucleotide, corresponding to non-coding strand DNA, encoded amino acids 725 to 733 and encoded 3' to codon 733 a HindIII restriction sequence. The resultant double stranded von Willebrand factor cDNA corresponding to the amino acid sequence from residue 441 to residue 733 (of the mature subunit) was then inserted, using EcoRI and HindIII restriction enzymes, into the double stranded replicative form of bacteriophage M13mp18 which contains a multiple cloning site having compatible EcoRI and HindIII sequences. Following the procedure of Kunkel, T.A., *Proc. Natl. Acad. Sci. USA,* 82, 488–492 (1985), site directed mutagenesis was performed using hybridizing oligonucleotides suitable for replacing all of the cysteine codons (residue positions 459, 462, 464, 471, 474, 509 and 695) with individual glycine codons (see Example 1) or, for example, 5 of the cysteine codons, residue positions 459, 462, 464, 471 and 474, with individual glycine codons (see Example 4). Mutant double stranded vWF cDNA fragments derived from the procedure were removed from M13mp18 phage by treatment with EcoRI and HindIII restriction endonucleases, after which the ends of the vWF cDNA fragments were modified with BamHI linkers.

The two types of mutant vWF cDNA, containing either 5 or 7 Cys to Gly mutations, were then separately cloned into the pET-3A expression vector (see Rosenberg, A.H. et al., *Gene,* 56, 125–136 (1987)) for expression from *E.coli* strain BL21(DE3), Novagen Co., Madison, WI. pET-3A vehicle containing cDNA for the vWF subunit fragment with 7 cysteine-to-glycine mutations is referred to as "p7E", and as "p5E" when the contained vWF cDNA fragment encoded the 5 above specified cysteine-to-glycine mutations. Mutant von Willebrand factor polypeptides produced by bacterial cultures containing expression plasmid p5E were compared with those expressed from cultures containing p7E plasmids. The p5E molecule is capable of forming a disulfide bond between cysteine residue 509 and 695 whereas the p7E molecule cannot.

The mutant polypeptides were not secreted by the bacterial host cells, but rather accumulated in poorly soluble aggregates ("inclusion bodies") from which the polypeptides were successfully solubilized following the procedure of Example 1 (p7E) and Example 4 (p5E). Polypeptides expressed from p7E and p5E plasmids were characterized by SDS-polyacrylamide gel electrophoresis and immunoblotting (Examples 2 and 5). Under reducing conditions both plasmids express polypeptide species having an apparent molecular weight of approximately 38,000 as measured by SDS-polyacrylamide gel electrophoresis, as would be predicted from the unglycosylated molecular weight of the expected amino acid sequences.

The behavior of p5E and p7E extracts was examined using immunological methods (see Example 5). vWF-specific murine monoclonal antibodies RG-46 and NMC-4 were used as probes. RG-46 has been demonstrated to recognize as its epitope a linear sequence of amino acids, comprising residues 694 to 708 within the mature von Willebrand factor subunit. The binding of this antibody to its determinant is essentially conformation independent. Mohri, H. et al., *J. Biol. Chem.,* 263(34), 17901–17904 (1988).

NMC-4 however, has as its epitope the domain of the von Willebrand factor subunit which contains the glycoprotein Ib binding activity. Mapping of the epitope has demonstrated that it is contained within two discontinuous domains (comprising approximately mature vWF subunit residues 474 to 488 and also approximately residues 694 to 708) brought into disulfide-dependent association, Mohri, H. et al., supra, although it could not be determined whether the disulfide bond conferring this tertiary conformation in the native vWF molecule was intrachain or interchain. Id. at 17903.

Accordingly, 7.5 μg samples (of protein) were first run on 10% SDS-polyacrylamide gels so that the antigenic behavior of particular bands (under reducing and nonreducing conditions) could be compared with results obtained by Coomassie blue staining. Immunoblotting ("Western Blotting") according to a standard procedure, Burnette, *A. Anal. Biochem.,* 112, 195–203 (1981), was then performed to compare p5E and p7E extracts.

It has been determined that, under nonreducing conditions, the single chain p5E polypeptide fragment (representing the sequence from residue 441 to residue 733) displays an approximate 120 fold increase in binding affinity for NMC-4 compared to the comparable cysteine-free species isolated from p7E. After electrophoresis under reducing conditions (utilizing 100 mM DTT), the single chain p5E species shows a remarkably decreased affinity for NMC-4, which was then very similar to that of the cysteine-free p7E species under either reduced or nonreduced conditions. NMC-4 also failed, under reducing or non-reducing conditions, to recognize as an epitope disulfide-linked dimers from the p5E extract.

The nitrocellulose filters used to produce autoradiographs based on NMC-4 were rescreened with RG-46 by subtracting the initial NMC-4 exposure response, which was kept low through a combination of low antibody titer and short exposure time. The binding of RG-46 to the 36,000 kDa p7E polypeptide on the filters was the same whether reducing or non-reducing conditions were chosen, consistent with the replacement of all cysteines by glycine in the expressed polypeptide.

A large molecular weight vWF antigen (reactive to RG-46) was present in the p5E polypeptide extract under nonreducing conditions. These p5E vWF aggregates (reflecting interchain disulfide bonds) migrated under reducing conditions in the same position as the p7E polypeptide indicating disruption of their disulfide contacts. However, the large p5E interchain disulfide aggregates which are readily recognized under nonreducing conditions by RG-46 were not recognized by NMC-4 under either reducing or nonreducing conditions. It was thus demonstrated that the disulfide bond between residues 509 and 695 in native multimeric vWF subunits represents an intrachain contact.

The disulfide bond between residues 471 and 474 of the mature vWF subunit has previously been shown to be an intrachain contact, thus the aforementioned embodiment is able to suggest that interchain disulfide bond(s) in multi-subunit mature vWF would be formed using one or more of cysteine residues 459, 462 or 464.

A wide variety of expression plasmids or viral expression vectors are suitable for the expression of the 441–733 fragment, or similar vWF fragments. Representative examples include pBR322, and derivatives thereof such as pET-1 through pET-7. Suitable host cells include the bacterial genuses of Escherichia and Bacillus. Of importance in the selection of an expression system is the recommended presence of a high efficiency transcription promoter directly adjacent to the vWF cloned DNA insert. Mutant vWF cDNA fragments may also be cloned in eucaryotic host cells.

This discovery is expected to be particularly useful in the design of therapeutic vWF polypeptides patterned upon the 52/48 tryptic fragment (for use as antithrombotics) or patterned instead upon the 116 kDa homodimer thereof (for use as antihemorrhagics).

Second Embodiment of the Invention

Many of the factors described above with respect to the design of and expression of therapeutic fragments of vWF from recombinant bacterial cells are applicable to the design of and expression of vWF fragments from eucaryotic host cells. Such applicability is readily apparent to those skilled in the art.

This second embodiment includes within its scope the recognition of certain of the roles performed by cysteine residues present in the residue 449–728 primary sequence fragment of the mature vWF subunit. In this connection, this embodiment confirms that the cysteine 509–695 disulfide bond is an intrachain bond and provides for effective therapeutics incorporating the 509–695 bond for the purpose of treating thrombosis, or for the purpose of treating von Willebrand's disease.

Both the antithrombotic polypeptides and antihemorrhagic polypeptides of this the second embodiment of the invention are based upon that amino acid sequence domain which comprises approximately residues 449 to 728 of the mature von Willebrand factor subunit and which, if fully glycosylated, would be equivalent in weight to the 52/48 kDa vWF subunit fragment. In practice it is difficult to derive therapeutically useful quantities of such polypeptides from blood plasma. Difficulties include effective separation of 116 kDa and 52/48 kDa fragments from other components of tryptic digests and effective sterilization of blood-derived components from human viruses such as hepatitis and AIDS. In addition, methods reported in the literature to generate the 52/48 kDa monomer from the 116 kDa dimer have utilized complete disulfide reduction with resultant loss of tertiary structure. Certain important manipulations of the 52/48 fragment, such as replacement of selective cysteine residues to improve product utility and stability, can only be accomplished in a practical sense by recombinant DNA technology.

However, the production by recombinant DNA-directed means of therapeutic vWF polypeptides analogous to the 52/48 tryptic fragment has met with certain limitations. It is desirable that the polypeptide not only be made by the host cells but that it be correctly folded for maximum therapeutic utility. It is believed that the principal factor which has to date prevented the expression of the most therapeutically active forms of the 52/48 fragment is the incorrect folding of the molecule caused by the linking up of cysteine residues to form incorrect disulfide contacts. In addition, such polypeptides appear to exhibit hydrophobic properties or solubility problems which would not be encountered if they were to be contained within the entirety of the natural vWF subunit, or were properly glycosylated.

Of critical importance, therefore, to the synthesis of vWF-derived therapeutic polypeptides is the selection of conditions which minimize the formation of improper disulfide contacts. Prior expression of such polypeptides from recombinant DNA in host bacterial cells has certain disadvantages. With reference to the first embodiment, newly produced vWF polypeptides are unable to escape from the host cells, causing them to be accumulated within insoluble aggregates therein (inclusion bodies) where the effective concentration of cysteine residues was extremely high. Under these circumstances, disulfide bonds not characteristic of the vWF molecule as it naturally exists in the plasma are encouraged to, and do, form either within the inclusion bodies or during attempts to solubilize the polypeptide therefrom.

This embodiment provides a solution to these difficulties by causing the vWF-derived polypeptides to be expressed in mammalian cells using a DNA sequence which encodes the polypeptide and which also encodes for a signal peptide, the presence of which causes the vWF polypeptide to be secreted from the host cells. Incorrect disulfide bond formation is minimized by limiting the accumulation of high local concentrations of the polypeptide as in inclusion bodies.

In addition, enzymes present in the host eucaryotic cells, unlike bacteria, are able to glycosylate (add carbohydrate chains to) the vWF-derived polypeptides resulting in therapeutic molecules which more closely resemble domains of vWF molecules derived from human plasma.

The recombinant 116 kDa polypeptide generated according to this embodiment, without mutation of any of the cysteine codons therefor, is demonstrated to represent a dimer of the subunit fragment consisting of residues 441–730 and possesses an amount of glycosylation equivalent to that found in the comparable region of plasma-derived vWF.

There follows hereafter a description of the types of therapeutic vWF-derived polypeptides which have or may be generated according to the effective recombinant procedures of the second embodiment.

Recombinant vWF Polypeptides of the Second Embodiment

Stated broadly, this second embodiment includes any fragment of mature von Willebrand subunit comprising that sequence of amino acids between approximately residue 449 and approximately residue 728, or a subfragment thereof, from which at least one of cysteine residues 459, 462 and 464 thereof is removed. Such removal reduces the tendency of the fragment to form undesired interchain disulfide bonds (and resultant dimers) with the result that therapeutic utility as an antithrombotic is improved.

A further aspect of the embodiment encompasses a glycosylated form of the above defined polypeptides.

In the design of certain antithrombotic polypeptides derived from the aforementioned region of vWF, it is preferred that cysteine residues be retained at positions 509 and 695 so that the tertiary structure of certain domains of the mature vWF subunit fragment that interact with GPIbαis preserved.

Also preferred in the practice of the embodiment is a glycosylated polypeptide derived from the aforementioned region of vWF in which cysteine residues are retained at positions 509 and 695 and in which each of cysteine residues 459, 462 and 464 is deleted or replaced by residues of other amino acids.

Additionally preferred in the practice of the embodiment is a glycosylated polypeptide derived from the aforementioned region of vWF in which cysteine residues are retained at positions 509 and 695 and in which any one of cysteine residues 459, 462 and 464 is deleted or replaced by a single residue of another amino acid.

Important factors involved in the design of, or further modification to, the preferred mutant polypeptides (antithrombotics) of the invention are described hereafter.

Potential binding sites for collagens and glycosaminoglycans (or proteoglycans) exist in the 449–728 tryptic fragment in the loop region between cysteine residues 509 and 695. In the event that binding at these sites by such macromolecules impairs the antithrombotic therapeutic utility of any of the recombinant polypeptides of the invention by, for example, also providing bridging to collagen, the polypeptide can be redesigned (for example, by proteolysis, covalent labelling or mutagenesis) to delete or alter the loop region, or a subdomain thereof.

There follows hereafter a discussion of means by which polypeptides of the second embodiment can be prepared and, in particular, by which such polypeptides can be effectively secreted from host cells in proper folded form and possessing preferably only those disulfide bonds whose presence is consistent with therapeutic utility.

Preparation of Mutant Polypeptides of the Second Embodiment—Construction of Suitable DNA Sequences and Expression Plasmids Essential elements necessary for the practice of the embodiment are: (A) a DNA sequence which encodes the residue 449–728 domain of the mature vWF subunit, or encodes a subdomain thereof; (B) an expression plasmid or viral expression vector capable of directing in a eucaryotic cell the expression therein of the aforementioned residue 449–728 domain, or subdomain thereof; and (C) a eucaryotic host cell in which said expression may be effected.

The expression of the DNA sequence of the von Willebrand factor subunit fragment is facilitated by placing a eucaryotic consensus translation initiation sequence and a methionine initiation codon upstream (5') to the residue 449–728 encoding DNA. The vWF DNA sequence may be a cDNA sequence, or a genomic sequence such as, for example, may be produced by enzymatic amplification from a genomic clone in a polymerase chain reation. Expression of the residue 449–728 encoding sequence is further facilitated by placing downstream therefrom a translation termination codon such as TGA. The vWF-polypeptide so expressed typically remains within the host cells because of the lack of attachment to the nascent vWF polypeptide of a signal peptide. In such a situation, purification of proteins expressed therein and the extraction of pharmacologically useful quantities thereof are more difficult to accomplish than if the polypeptide were secreted into the culture medium of the host cells. Such expression systems are nonetheless useful for diagnostic assay purposes such as, for example, testing the proper function of platelet GPIb-IX receptor complexes in a patient.

In the preferred practice of the invention in which the polypeptide is secreted from the host cell, there is provided a vWF-encoding DNA sequence for insertion into a suitable host cell in which there is also inserted upstream from the residue 449–728 encoding sequence thereof a DNA sequence encoding the vWF signal peptide (see Example 7). Other vWF-encoding DNA sequences corresponding to different regions of the mature vWF subunit, or corresponding to the propeptide, or to combinations of any of such regions, may be similarly expressed by similarly placing them downstream from a vWF signal peptide sequence in a suitable encoding DNA. When attached to the amino terminal end of the residue 449–728 fragment of the vWF subunit, the signal peptide causes the fragment to be recognized by cellular structures as a polypeptide of the kind to be processed for ultimate secretion from the cell, with concomitant cleavage of the signal polypeptide from the 449–728 fragment.

With respect to the construction of a eucaryotic expression system and the expression therein of the tryptic 52/48 kDa domain of mature subunit vWF (the residue 449–728 fragment), it has been found (see Example 7) to be conveneint to manipulate a slightly larger fragment represented by residues 441 (arginine) to 730 (asparagine). Other similar fragments containing small regions of additional amino acids (besides the 449–728 residue sequence), which additional amino acids do not significantly affect the function of said fragment, may also be expressed.

Similarly, functional fragments may be expressed from which, when compared to the 449–728 fragment, several residues adjacent to the amino and carboxy terminals have been removed as long as the GPIb($\alpha$) binding sequences are not compromised.

It has also been found to be effective, with respect to the construction of a suitable DNA sequence for encoding and expressing the residue 441–730 fragment, to cause to be inserted between the DNA encoding the carboxy terminus of the signal peptide and the codon for residue 441, codons for the first three amino acids of the vWF propeptide (alanine-glutamic acid-glycine) said codons being naturally found directly downstream (3') to the signal sequence in the human vWF gene. As is further elaborated below (see Example 17), the presence of such a propeptide sequence (a spacer) facilitates recognition by signal peptidase of a proper cleavage site which process generates a therapeutic vWF polypeptide of a proper size and facilitates secretion from the host cell of the therapeutic product. As elaborated below, this spacer sequence should be of semipolar or polar character.

In accordance with this invention, there is provided a spacer sequence comprising between one and up to the first ten residues of the amino terminal region of the vWF propeptide. It is within the scope of the invention to utilize longer propeptide encoding sequences with the understanding that the desired tertiary structure of the 441–730 residue sequence is not adversely affected.

A wide variety of expression plasmids or viral expression vectors are suitable for the expression of the residue 441–730 mature vWF subunit fragment or similar vWF fragments. One factor of importance in selecting an expression system is the provision in the plasmid or vector of a high efficiency transcription promoter which is directly adjacent to the cloned vWF insert.

Another factor of importance in the selection of an expression plasmid or viral expression vector is the provision in the plasmid or vector of an antibiotic resistance gene marker so that, for example, continuous selection for stable transformant eucaryotic host cells can be applied.

Examples of plasmids suitable for use in the practice of the invention include pCDM8, pCDM8$^{neo}$, pcDNA1, pcDNA1$^{neo}$, pMAM$^{neo}$ and Rc/CMV. Preferred plasmids include pCDM8$^{neo}$, pcDNA1$^{neo}$, pMAM$^{neo}$ and Rc/CMV.

Examples of viral expression vector systems suitable for the practice of the invention include those based upon retroviruses and those based upon baculovirus *Autographa californica* nuclear polyhedrosis virus.

Representative host cells comprising permanent cell lines suitable for use in the practice of the invention include CHO-K1 Chinese hamster ovary cells, ATCC-CCL·61; COS-1 cells, SV-40 transformed African Green monkey kidney, ATCC-CRL 1650; ATT 20 murine pituitary cells; RIN-5F rat pancreatic $\beta$ cells; cultured insect cells, *Spodoptera frugiperda*; or yeast (Sarcomyces).

Example 7 contains a detailed explanation of preferred procedures used to express and secrete the 441–730 sequence. In that Example, the fragment is secreted as a homodimer held together by one or more disulfide bonds involving cysteine residues 459, 462 and 464. Expression of monomeric fragments useful as antithrombotics necessitates control be made of the disulfide bonding abilities of the monomers which is achieved most preferably by mutagenesis procedures as described in the aforementioned First Embodiment of the Invention.

The specific protocol used to generate the mutant vWF residue 441–730 fragment containing cysteine to glycine substitutions at each of residue positions 459, 462 and 464 is described in Example 8. The expression plasmid used therein was designated pAD4/Δ3C.

The specific protocol, adapted from that of Example 8, and which was used to generate the three mutant residue 441–730 fragments, each of which contains a different single Cys→Gly mutation (at positions 459, 462 or 464) is described in Example 10. The respective expression plasmids used therein were designated pAD4/G$^{459}$, pAD4/G$^{462}$ and pAD/G$^{464}$ (collectively "the pAD4/Δ1C plasmids"). Similar procedures may be used to produce mutant residue 441–730 fragments with Cys→Gly mutations at two of the three aforementioned positions.

Properties of the Polypeptides of the Second Embodiment

Homodimeric 116 kDa vWF Fragments

Example 7 below discloses the use of stably transformed CHO-K1 cells to express the unmutagenized residue 441–730 vWF subunit fragment. As set forth in Example 10 below, the unmutagenized fragment was also expressed in unstable COS-1 transformants.

SDS-polyacrylamide gel electrophoresis of secreted and immunoprecipitated proteins derived from CHO-K1 cells demonstrates that, under nonreducing conditions, the dominant vWF-derived polypeptide, detected by staining with Coomassie blue, has an apparent molecular weight of about 116,000 (Example 7). This result was confirmed by characterizing the polypeptides secreted by pAD4/WT transformed COS-1 cells (Example 11) using autoradiographs of $^{35}$S-labelled proteins. Under disulfide-reducing conditions (such as in the presence of 100 mM dithiothreitol) the 116 kDa fragment was no longer detected and the vWF-derived material appears as the expected 52/48 kDa monomer.

The apparent molecular weight of the recombinant 116 kDa polypeptide was consistent with the presence of said polypeptide as a homodimer of the 441–730 fragment. This homodimer carries also an amount of glycosylation equivalent to that observed in the 116 kDa polypeptide isolated by tryptic digestion of mature plasma (circulating) vWF. It is thus demonstrated that expression of the 441–730 fragment in the mammalian cell cultures of this invention favors the formation of the disulfide-dependent 116 kDa dimer thereof, mimicking the structure seen in plasma. That the 116 kDa fragment so formed represents a correctly folded polypeptide was evidenced by its reaction (under nonreducing conditions) with conformation-dependent NMC-4 antibody. This antibody recognizes a properly assembled GPIb(α) binding site. Reactivity with NMC-4 disappears under reducing conditions.

Since it was demonstrated in the first embodiment (using bacterially-expressed vWF fragments) that cysteine residues 471 and 474 and also residues 509 and 695 are involved in intrachain bonds, the interchain bonds which stabilize the 116 kDa homodimer must be formed from one or more of residues 459, 462 and 464. It is further noted that since residues 459, 462 and 464 are in such close proximity in any monomer, there may be variation as to which particular residue or residues contribute the interchain disulfide bond or bonds which form the interpolypeptide contact in any particular mature vWF dimer or multimer, or recombinant 116 kDa fragment. Therapeutically-active populations of dimeric molecules can be generated according to the practice of the invention utilizing any of the possible combinations of interchain disulfide bonds.

It is noted that it is also possible that some structural folding or disulfide bond formation associated with the generation of therapeutically active conformations of the recombinant 116 kDa dimers of the invention, or disulfide exchange therein, occurs after the polypeptides are secreted from a host cell.

Since there are also contained within the 441–730 vWF fragment potential binding sites for collagens, proteoglycans and glycosaminoglycans, the 116 kDa polypeptide is capable of performing a bridging function between a platelet and the subendothelium. This enables it to be used in a method for inducing platelet adhesion to surfaces such as, for example, vascular subendothelium. There is also provided a method of inducing platelet activation and/or aggregation which comprises contacting platelets with an effective amount of the recombinant 116 kDa polypeptide. Such a method is useful in the treatment of von Willebrand disease.

It is noted that as long as at least one of the one or more potential interchain disulfide bonds stabilizing the homodimer is left intact, and the amino acid sequences comprising the two GPIb(α) binding sites are preserved, that other regions of one or more of the two monomeric fragments thereof could be deleted, if necessary, to modify the therapeutic properties of the dimer.

52/48 kDa Monomeric vWF Fragments

An important aspect of the second embodiment of the invention is the provision of glycosylated 52/48 kDa monomeric fragments of the vWF subunit having substantial elements of normal tertiary structure. Such fragments have a reduced tendency to form dimers which tend to be unsuitable for use as antithrombotic therapeutics.

Following the above described procedures for site directed mutagenesis, residue 441–730 vWF fragments were produced in which one or more of cysteine residues 459, 462 and 464 were replaced with glycine residues. Examples 8, 9 and 10 below explain the mutagenesis and cell culture conditions necessary to create COS-1 cell transformants expressing these mutant vWF polypeptides. Examples 11 to 13 of the invention describe the properties of the molecules so derived in comparison with the recombinant 116 kDa polypeptide produced from pAD4/WT transformed COS-1 cells.

The vWF-derived polypeptides expressed by pAD4/Δ3C transformed COS-1 cells (containing the vWF 441–730 DNA sequence, but with each of cysteine codons 459, 462 and 464 thereof replaced by single glycine codons) were compared with the polypeptides secreted by pAD4/WT transformed COS-1 cells. To perform the comparisons, $^{35}$S-methionine-supplemented culture medium from each culture was subjected to immunoprecipitation using equal amounts of NMC-4 and RG-46 anti-vWF antibodies (Example 11) to collect the vWF-derived secreted proteins. The immunoprecipitated vWF polypeptides were then resolved by autoradiography of $^{35}$S-label on SDS polyacrylamide gels. No 116 kDa polypeptide could be detected in culture extracts of pAD4/Δ3C transformed cells under nonreducing conditions. Instead, under either reducing or nonreducing conditions, a band having an apparent molecular weight of 52 kDa was seen. In contrast, the pAD4/WT transformed COS-1 cells produce under nonreducing conditions, as expected, a polypeptide of apparent molecular weight of 116 kDa.

The immunoprecipitation procedure was also repeated using only conformation-dependent NMC-4 antibody (Example 12). The major vWF-derived component isolated from the culture medium of pAD4/WT transformed cells again had an apparent molecular weight of 116 kDa under nonreducing conditions and 52 kDa under reducing conditions. A band of apparent 52 kDa molecular weight was detected under nonreducing conditions on gels of pAD4/Δ3C derived polypeptide material. As described in Example 12, reactivity with NMC-4 antibody is important evidence that the 52 kDa fragment detected in pAD4/Δ3C transformed cells possesses the tertiary structure of the natural residue 441–730 domain.

The immunoprecipitation procedure was also used to detect NMC-4 reactive vWF polypeptide produced by pAD4/Δ1C transformed COS-1 cells cultured under conditions similar to those for pAD4/WT and Δ3C transformants in the presence of $^{35}S$ methionine. Immunoprecipitated proteins were run under reducing and nonreducing conditions in SDS-polyacrylamide gels and compared with vWF polypeptides produced by pAD4/WT and pAD4/Δ3C transformants (Example 13).

It was revealed that substitution of any one of cysteine residues 459, 462 or 464 by glycine results predominantly in a polypeptide having an apparent molecular weight of 52 kDa under nonreducing or reducing conditions, the formation of the 116 kDa species having been prevented.

The apparent molecular weight of 52 kDa for recombinant polypeptides derived from COS-1 cells transformed with either pAD4/Δ3C or pAD4/Δ1C plasmids is consistent with said polypeptides being monomers of the 441–730 fragment, while carrying also an amount of glycosylation equivalent to that seen in the 52 kDa polypeptide as isolated from tryptic digestion and reduction of mature plasma (circulating) vWF.

Unlike the dimeric polypeptides of apparent 116 kDa molecular weight, the monomeric 52 kDa polypeptides produced by pAD4/Δ1C and pAD4/Δ3C plasmids are unlikely to be capable of the bridging function associated with the dimer. Accordingly, there is provided a method of preventing platelet activation and/or aggregation which comprises contacting platelets with an effective amount of a mutant recombinant 52/48 kDa polypeptide which polypeptide shows at least a substantially reduced tendency to dimerize when compared with nonmutant (wild type) recombinant 52/48 kDa polypeptides.

There is further provided a method of preventing the adhesion of platelets to surfaces which comprises contacting platelets with an effective amount of a mutant recombinant 52/48 kDa polypeptide which shows at least a substantially reduced tendency to dimerize when compared with nonmutant recombinant 52/48 kDa polypeptides.

Contained within the 441–730 vWF fragment are potential binding sites for collagen (approximately residues 542–622) and glycosaminoglycans and proteoglycans (also within the residue 509–695 disulfide loop), in addition to the GPIbα binding sites. It is probable because of steric considerations that a single fragment comprising residues 441–730 could not perform effectively as a bridging, potentially thrombotic, molecule. It is noted, however, that as long as the GPIb(α) binding domain of the 52/48 kDa monomer (consisting of approximately the primary sequence regions 474–488 and 694–708, and a tertiary domain thereof contributed in part by the 509–695 disulfide bond) is preserved, other regions (such as part of the heparin and collagen binding loop) of the said 52/48 kDa monomeric fragment could be deleted or altered, such as by proteolysis or by mutagenesis, if necessary, to modify or preserve the antithrombotic therapeutic properties thereof.

It is also possible that some structural folding or disulfide bond formation associated with the generation of therapeutically active conformations of the recombinant 52/48 kDa monomers of the invention, or disulfide exchange therein, occurs after the polypeptides are secreted from a host cell.

The Present (Third) Embodiment of the Invention

This invention defines a series of polypeptides that correspond to amino acid sequences (domains) of mature von Willebrand factor subunit. The polypeptides are capable of inhibiting the binding of platelet glycoprotein Ibα to von Willebrand factor, and accordingly, have utility as antithrombotics.

Fugimura, Y. et al., *J. Biol. Chem.,* 261, 381–385 (1986) defined a reduced and alkylated fragment of mature von Willebrand factor subunit beginning at amino acid residue $Val^{449}$ that contained the domain of said protein interacting with glycoprotein Ibα. The domain was further characterized, Fugimura, Y. et al., *J. Biol. Chem.,* 262, 1734–1739 (1987), to have its carboxy terminus at residue $Lys^{728}$. Mohri, H. et al., *J. Biol. Chem.,* 263, 17901–17904 (1988) determined that a GPIbα binding domain of vWF was formed by two discontinuous sequences, $Cys^{474}$-$Pro^{488}$ and $Leu^{694}$-$Pro^{708}$, contained within said fragment, maintained in a proper conformation in native vWF by disulfide bonding, although the authors were unable to identify the cysteine residues which formed the stabilizing bonds and whether said bonds were intrachain or interchain. It has subsequently been determined that an intrachain disulfide bond (cysteine 509–695) is important in regulating the function of the two discontinuous binding sequences. Additional regions (domains) within the 449–728 tryptic fragment of vWF that affect its interaction with platelet glycoprotein Ibα and thereby have utility in the design of antithrombotic polypeptides have been identified. In particular, it has been determined that modification of the intrachain disulfide loop (between $Cys^{509}$ and $Cys^{695}$) regulates the affinity of vWF for glycoprotein Ibα. Ware, J. et al., *Proc. Natl. Acad. Sci. USA,* 88, 2946–2950 (1991) have identified a point mutation in a patient suffering from Type IIb von Willebrand disease which enhanced the affinity of von Willebrand factor for platelet membrane glycoprotein Ibα. The identified mutation, $Trp^{550}$ to $Cys^{550}$, occurs within the $Cys^{509}$ to $Cys^{695}$ loop region of vWF. Cooney, K.A. et al., *Blood,* 76 (supp. 1) Abstract 1661, page 418a, Nov. 15, 1990 identify additional Type IIb phenotypic mutations, $Arg^{543}$ to $Trp^{543}$ and $Val^{553}$ to $Met^{553}$ from the loop. Further additional mutations from patients having Type II von Willebrand disease, or Type IIb-like symptoms include loop mutations $Arg^{511}$ to $Trp^{511}$ and $Gly^{561}$ to $Asp^{561}$.

Described herein (Examples 14–17) are experiments to define the identity of domains of a 449–728 fragment of von Willebrand factor polypeptide having antithrombotic utility. Example 15 of the invention describes procedures of site-directed or loopout mutagenesis whereby DNA sequences encoding, for example, a 441–733 residue fragment of von Willebrand factor subunit, were used to produce DNA subsequences that encode antithrombotic domains of said von Willebrand factor fragment.

The following are among the polypeptides that were produced according to these procedures: (A) polypeptides consisting of the residue 441–733 sequence, but lacking either internal residue 474–488 or residue 694–708 subsequence; (B) additional polypeptide domains of the aforementioned fragment comprising N-terminal deletions, for example, $Gly^{475}$-$Val^{733}$, $Thr^{492}$-$Val^{733}$ and $Tyr^{508}$-$Val^{733}$; (C) polypeptides comprising C-terminal deletions, that is, having an amino terminus at $Arg^{441}$, but having carboxy termini at, for example, residues $Asp^{709}$, $Pro^{704}$, $Glu^{700}$ and $Asp^{696}$; and (D) a final class of polypeptides comprising domains in which there have been both N-terminal and also C-terminal deletions.

Antithrombotic polypeptides representative of this embodiment of the invention are shown in FIG. 2. The polypeptides of the invention comprise one to three domains and share a sequence of amino acids corresponding to that domain of mature von Willebrand factor subunit having an amino terminus at about $Cys^{509}$ and a carboxy terminus at about $Cys^{695}$. Polypeptides containing this domain occur in two forms; those containing a 509–695 intrachain disulfide bond, and those molecules which lack the disulfide bond. Typically, maintenance of the reduced form requires reduction and then chemical alkylation of the cysteines, or substitution therefore by other amino acids based on modification of an encoding DNA.

Additional polypeptides of the invention comprise the aforementioned $Cys^{509}$-$Cys^{695}$ domain and comprise also, attached to the amino terminus of said domain, an additional "second" domain comprising a sequence of amino acids corresponding to that fragment of mature von Willebrand factor subunit having its amino terminus at or about $Arg^{441}$ and a carboxyl terminus at about $Tyr^{508}$, or a subfragment or combination of subfragments thereof.

Additional polypeptides of the invention comprise the aforementioned $Cys^{509}$-$Cys^{695}$ domain and comprise also, attached to the carboxy terminus of said $Cys^{509}Cys^{695}$ domain, a third, or "other domain" of amino acid sequence corresponding to that fragment of mature von Willebrand factor subunit having its amino terminus at about $Asp^{696}$ having its carboxy terminus at about $Val^{733}$, or a subfragment or combination of subfragments thereof.

An additional type of polypeptide of the invention comprises a domain contributed by the sequence of amino acids from $Cys^{509}$-$Cys^{695}$, and polypeptides contributed by both the second and third aforementioned domains.

The polypeptides of the invention were tested in in vitro assays indicative of potential antithrombotic activity. A discussion of the properties of the polypeptides of the invention is provided in Examples 14 to 17.

Antibodies with Therapeutic Activity

Antibodies, and particularly conformation dependent antibodies, are powerful tools for analyzing the structure and function of macromolecules. By blocking macromolecular interactions, antibodies can also have important therapeutic utility.

Accordingly, this invention includes within its scope an antibody which is specific for the vWF subunit, or any polypeptide containing a subset thereof which antibody is made by a process which involves immunizing animals with one or more polypeptides defined by the invention.

Therapeutic compositions

One or more of the polypeptides of the present invention can be formulated into pharmaceutical preparations for therapeutic, diagnostic, or other uses. To prepare them for intravenous administration, the compositions are dissolved in water typically containing also one or more physiologically compatible substances such as sodium chloride. There results a solution having a pH, ionic strength, and osmotic potential compatible with therapeutic use (the range of potential solute concentrations being well known in the art, or readily determined), said water and physiologically compatible substances comprise a pharmaceutically acceptable carrier.

With respect to the therapeutic use of the polypeptides of the invention, the amount to administer for the prevention or inhibition of thrombosis will depend upon the affinity of the polypeptide for GPIbα in vivo, and/or for other macromolecules that participate in hemostasis and thrombosis in the body, on the lifetime of the polypeptide in the body, and on the severity with which the patient is subject to thrombosis. Said amount can be determined readily for any particular patient.

It is also within the practice of the invention to provide a therapeutic composition containing one or more of the polypeptides of the invention and also additional therapeutic substances. Such additional substances include heparin and other anticoagulants, aspirin or other antiplatelet drugs, or tissue plasminogen activator or other prefibrinolytic drugs.

EXAMPLES

The following Examples are representative of the practice of the invention.

Example 1

Expression of a mutant cysteine-free mature von Willebrand factor subunit fragment having an amino terminus at residue 441 (arginine) and a carboxy terminus at residue 733 (valine)

Preparation of a cDNA Clone from pre-pro-von Willebrand Factor mRNA

A cDNA clone encoding the entire von Willebrand factor gene (for the pre-propeptide) was provided by Dr. Dennis Lynch, Dana-Farber Cancer Institute, Boston, MA and was prepared as described in Lynch, D.C. et al., *Cell*, 41, 49–56 (1985). It had been deemed probable that the size of vWF mRNA would likely exceed that of human 28S type rRNA. Accordingly, total RNA from endothelial cells (the major source of plasma vWF) was sedimented in sucrose gradients, with RNA larger than 28S being selected for construction of a cDNA library.

This enriched fraction was further purified using two separate cycles of poly(u)-Sephadex® chromatography to select for RNA species (mRNA) having 3' polyadenylated ends. Lynch et al., supra, estimated the prevalence of vWF mRNA in this fraction at about 1 in 500, which fraction was used to generate a cDNA library of approximately 60,000 independent recombinants.

To generate the cDNA library, standard techniques were used. The mRNA population was primed using an oligo (dT) primer, and then transcribed with a reverse transcriptase. The RNA strands were then removed by alkaline hydrolysis, leaving cDNA anticoding strands (equivalent to transcribed strands) which were primed by hairpin looping for second strand synthesis using DNA polymerase I. The hairpin loop was removed with SI nuclease and rough ends were repaired with DNA polymerase I.

GC tailing, Maniatis, T. et al., *Molecular Cloning*, 2nd ed., v.1, p.5.56 (1987), was then used to anneal the cDNA into plasmid vector pBR322. Oligo(dC) tails were added to the cDNA fragments with terminal transferase and were annealed to oligo(dG) tailed pBR322. The plasmids were transformed into ampicillin sensitive *E.coli*, strain HB101 for propagation. Suitable clones were identified after screening with $^{32}$P-labelled cDNA prepared as reverse transcriptase product of immunopurified vWF polysomes. Positive clones were subcloned into pSP64 (Promega Co., Madison, WI).

Primer Directed Amplification of cDNA cDNA representing the full length pre-pro-vWF gene from pSP64 was subjected to enzymatic amplification in a polymerase chain reaction. Based upon the established nucleotide sequence of the pre pro-vWF gene, Bonthron, D. et al. *Nucl. Acids Res.*, 14(17), 7125–7127 (1986); Mancuso, D. et al., *J. of Biological Chemistry*, v.264(33), 19514-19527 (1989) oligonucleotides flanking the region of interest (designated (1), SEQ ID NO: 2, and (2), SEQ ID NO: 3) were prepared. All oligonucleotides used herein were synthesized by the phosphoramidite method, Sinha, et al.,

*Tetrahedron Letters,* 24, 5843 (1983), using a model 380B automated system, Applied Biosystems, Foster City, Calif.

```
Oligonucleotide (1) (SEQ ID NO: 2)
           5'ACGAATTC CGG CGT TTT GCC TCA GGA3'
               EcoRI  Arg441                Gly446
Oligonucleotide (2) (SEQ ID NO: 3)
3'GG GAC CCC GGG TTC TCC TTG AGG TAC CAT TCGAAG5'
5'CC ctg ggg ccc aag agg aac tcc atg gta agcttc3'
    Leu725                        Met732Val733HindIII
```

The oligonucleotides overlap the ends of the coding region for that fragment of the mature vWF subunit which can be produced by digestion with trypsin and which begins with residue 449 (valine) and ends with residue 728 (lysine). Oligonucleotide (1) corresponds to coding strand DNA (analogous with mRNA) for amino acid positions 441 to 446 and adds an EcoRI restriction site 5' to the codon for amino acid 441. Oligonucleotide (2) corresponds to the non-coding strand (transcribed strand) of mature vWF DNA for amino acids positions 725–733 and adds a HindIII restriction site 3' to the codon for amino acid 733. The coding strand complementary to (2) is shown in lower case letters.

Using the above oligonucleotides with the full length cDNA as template, a cDNA fragment corresponding to mature vWF residues Nos. 441–733, and containing EcoRI and Hind III linkers, was then synthesized in a polymerase chain reaction following the method of Saiki, R.K. et al. *Science,* 239, 487–491 (1988).

The procedure utilizes a segment of double-stranded vWF cDNA, a subsegment of which is to be amplified, and two single-stranded oligonucleotide primers (in this case oligonucleotides (1), (2)) which flank the ends of the subsegment. The primer oligonucleotides (in the presence of a DNA polymerase and deoxyribonucleotide triphosphates) were added in much higher concentrations than the DNA to be amplified.

Specifically, PCR reactions were performed with a DNA thermal cycler (Perkin Elmer Co., Norwalk, CT/Cetus Corporation, Berkeley, CA) using Taq polymerase (*Thermus aguaticus*). The reactions were run in 100 µλ volumes containing 1.0 µg of pre-pro-vWF cDNA, 1.0 µg of each synthetic oligonucleotide primer, and buffer consisting of 50 mM KCl, 10 mM Tris·HCl (pH 8.3), 1.5 mM $MgCl_2$, 0.1% gelatin (BioRad Co., Richmond, CA) and 200 mM of each dNTP. PCR conditions were 35 cycles of 30 seconds at 94° C., 30 seconds at 52° C. and 1 minute at 72° C. Amplified fragments were then purified and isolated by electrophoresis through a 2% agarose gel, Maniatis et al., *Molecular Cloning, A Laboratory Manual,* 164–170, Cold Spring Harbor Lab., Cold Spring Harbor, NY (1982).

The vast majority of polynucleotides which accumulate after numerous rounds of denaturation, oligonucleotide annealing, and synthesis, represent the desired double-stranded cDNA subsegment suitable for further amplification by cloning.

For some experiments, cDNA corresponding to the mature vWF fragment beginning at amino acid sequence position 441 and ending at position 733 was prepared and amplified directly from platelet mRNA following the procedure of Newman, P.J. et al. *J. Clin. Invest.,* 82, 739–743 (1988). Primer nucleotides No. 440 and 733 were utilized as before with the resulting cDNA containing EcoRI and HindIII linkers.

Insertion of cDNA into M13mp18 Cloning Vehicle The resultant double stranded von Willebrand factor cDNA corresponding to the amino acid sequence from residue 441 to 733 was then inserted, using EcoRI and HindIII restriction enzymes, into the double stranded replicative form of bacteriophage M13mp18 which contains a multiple cloning site having compatible EcoRI and HindIII sequences.

M13 series filamentous phages infect male (F factor containing) *E.coli* strains. The infecting form of the virus is represented by single stranded DNA, the (+) strand, which is converted by host enzymes into a double stranded circular form, containing also the minus (−) strand, which double stranded structure is referred to as the replicative form (RF). The ability to isolate a stable single stranded (+) form of the virus is particularly useful to verify the integrity of any cloned sequences therein. See Messing, J., *Meth. Enzymology,* 101, 20–78 (1983); Yanish-Perron, C. et al., *Gene,* 33, 103–109 (1985).

Accordingly, the vWF cDNA insert was completely sequenced using single-stranded dideoxy methodology (Sanger, F. et al. *Proc. Natl. Acad. Sci USA,* 74, 5463–5467 (1977)), utilizing the single-stranded (+) form of M13mp18, to confirm that the vWF cDNA fragment contained the correct coding sequence for mature vWF subunit residues 441–733.

Site-Directed Mutagenesis to Replace Cysteine Residues

Cysteine residues 459, 462, 464, 471, 474, 509, and 695, within the mature vWF fragment corresponding to amino acids 441 to 733, were replaced with glycine residues by substitution of glycine codons for cysteine codons in the corresponding cDNA. In order to accomplish this, oligonucleotides (see Sequence Listing ID NOS: 5–8) encompassing the region of each cysteine codon of the vWF cDNA were prepared as non-coding strand (transcribed strand) with the corresponding base substitutions needed to substitute glycine for cysteine. The oligonucleotides used were as follows:

Oligonucleotide (3) (SEQ ID NO: 4)
3'GGA CTC GTG CCG GTC TAA CCG GTG CAA CTA CAA CAG5'
5'cct gag gac ggc cag att ggc cac ggt gat gtt gtc3'
  Pro Glu His Gly Gln Ile Gly His Gly Asp Val Val
           459         462         464
(simultaneously replacing cysteines 459, 462, 464).
Oligonucleotide (4) (SEQ ID NO: 5)
  3'TTG GAG TGG CCA CTT CGG CCG GTC CTC GGC5'
  5'aac ctc acc ggt gaa gcc ggc cag gag ccg3'
    Asn Leu Thr Gly Glu Ala Gly Gln Glu Pro
                   471         474
(simultaneously replacing cysteines 471, 474)
Oligonucleotide (5) (SEQ ID NO: 6)
  3'CTA AAG ATG CCG TCG TCC G5'
  5'gat ttc tac ggc agc agg c3'
    Asp Phe Tyr Gly Ser Arg
                 509
(replacing cysteine 509)
Oligonucleotide (6) (SEQ ID NO: 7)
  3'TCG ATG GAG CCA CTG GAA CGG5'
  5'agc tac ctc ggt gac ctt gcc3'
    Ser Tyr Leu Gly Asp Leu Ala
                 695
(replacing cysteine 695)

Hybridizing oligonucleotides are shown in capital letters and are equivalent to the transcribed strand (non-coding DNA). The equivalent coding strand is shown in lower case letters with the corresponding amino acids shown by standard three letter designation (for designations see Table 1).

As elaborated below, cysteines 459, 462 and 464 were replaced simultaneously using oligonucleotide (3). Cysteine residues 471 and 474 were then replaced simultaneously using oligonucleotide (4). Cysteine residues 509 and 695 were then replaced individually using oligonucleotides (5) and (6) respectively.

The cysteine to glycine cDNA substitutions were accomplished following the procedure of Kunkel, T.A., *Proc. Natl. Acad. Sci. USA*, 82,488–492 (1985) which procedure repeats a series of steps for each oligonucleotide and takes advantage of conditions which select against a uracil containing DNA template:

(A) M13mp18 phage, containing wild type vWF cDNA corresponding to amino acid positions 441 to 733, is grown in an *E.coli* CJ236 mutant dut⁻ung⁻strain in a uracil rich medium. Since this *E.coli* strain is deficient in deoxyuridine triphosphatase (dut⁻), an intracellular pool of dUTP accumulates which competes with dTTP for incorporation into DNA. (see Shlomai, J. et al. *J. Biol. Chem.*, 253(9), 3305–3312 (1978). Viral DNA synthesized under these conditions includes several uracil insertions per viral genome and is stable only in an *E.coli* strain which is incapable of removing uracil, such as (ung⁻) strains which lack uracil glycosylase. Uracil-containing nucleotides are lethal in 59 single stranded (⁺) M13mp18 DNA in ung⁺ strains due to the creation of abasic sites by uracil glycosylase.

(B) Single-stranded (⁺) viral DNA is isolated from culture media in which phage were grown in *E.coli* strain CJ236 dut⁻ung⁻. The single stranded (⁺) form of the virus contains the specified vWF cDNA at its multiple cloning site which cDNA is equivalent to the nontranscribed vWF DNA strand.

(C) Oligonucleotide (3), which contains codon alterations necessary to substitute glycines for cysteines at positions 459, 462 and 464, is then annealed in vitro to single stranded (⁺) phage DNA. Generally, a wide range of oligonucleotide concentrations is suitable in this procedure. Typically 40 ng of oligonucleotide was annealed to 0.5–1.0 μg M13mp18 phage (⁺) DNA.

(D) All missing sequence of the M13mp18(⁻) strand is then completed in vitro using $T_7$ DNA polymerase and $T_4$ DNA ligase in a dTTP rich environment thereby generating a transcribable vWF cDNA sequence corresponding to amino acid positions 441 to 733 of the mature vWF subunit.

(E) The double stranded M13mp18 phage, now containing a thymine normal (⁻) strand and a (⁺) strand with several uracil substitutions, is transformed into a wild type *E.coli* XL-1 Blue (Stratagene, La Jolla, CA) strain which contains normal levels of uracil glycosylase and deoxyuridine triphosphatase.

(F) Uracil glycosylase and other enzymes present in the new host initiate destruction of the uracil-containing (⁺) strand of the double-strand phages, leading after replication in the host of remaining phage (⁻) strand DNA to the presence of stable thymine-normal double stranded (RF) DNA which reflects the glycine mutations induced by the oligonucleotide.

(G) Steps (A) to (F) of the above process are then repeated for each of oligonucleotides (4), (5) and (6) until each successive cysteine codon of the vWF sequence within the M13mp18 phage has been replaced by a glycine codon.

(H) Upon completion of mutagenesis procedures the sequence of the vWF cDNA insert was reconfirmed using the single stranded DNA dideoxy method. (Sanger, F. et al., supra)

Construction of Expression Plasmids

The double stranded vWF cDNA fragment containing 7 site-specific cysteine to glycine mutations is then removed from M13mp18 phage by treatment with EcoRI and HindIII restriction endonucleases, after which the ends of the fragment are modified with BamHI linkers (Roberts, R.J. et al. *Nature*, 265, 82–84 (1977)) for cloning into a high efficiency *E.coli* expression vector. The particular expression vector chosen is plasmid pET-3A, developed by Rosenberg, A.H. et al. *Gene*, v.56, 125–135, (1987) and which is a pBR322 derivative containing a high efficiency (φ10) T7 transcription promoter directly adjacent to the BamHI linker site. When containing the above-specified fragment of mutant vWF cDNA, the pET-3A vehicle is refered to as "p7E" or p7E expression plasmid.

A second pET-3A-derived expression plasmid (designated p7D) was constructed containing the identical vWF coding sequence cloned into the plasmid in the opposite orientation. p7D should be unable to express the vWF polypeptide fragment.

A third expression plasmid (pJD18) contains wild type 52/48 tryptic vWF fragment cDNA encoding the vWF amino acid sequence between residues 441 and 733, (with 7 cysteines) in the same pET-3A vector.

The p7E (or p7D and pJD18) expression plasmids were then cloned into an ampicillin sensitive *E.coli* strain, BL21 (DE3), Novagen Co., Madison WI, according to a well established protocol Hanahan, D., *J. Mol. Biol.*, 166, 557–580 (1983). Strain BL21(DE3) is engineered to contain a gene for T7 RNA polymerase so that the vWF insert can be transcribed with high efficiency.

Expression of Mutant vWF Polypeptides

Three separate samples of *E.coli* strain BL21(DE3) containing respectively p7E, p7D or pJD18 expression plasmids were innoculated into 5–6 ml of 2X-YT growth medium containing 200 μg/ml of ampicillin, and grown overnight at 37° C. to create fully grown cultures. 2X-YT growth medium contains, per liter of water, 10 gm Bacto-tryptone, 10 gm yeast extract and 5 gm NaCl. Five ml of each overnight culture was then innoculated into 500 ml of 2X-YT medium, again containing 200 μg/ml of ampicillin and grown for 2 hours at 37° C. with shaking.

After the 2 hour incubation period, the cultures were induced for protein expression by addition of isopropyl-beta-d-thiogalactopyranoside to a concentration of 5 mM. The incubation was then continued for 3 hours at 37° C.

A high level of expression of vWF polypeptide was obtained with p7E and pJD18 resulting in the generation of cytoplasmic granules or "inclusion bodies" which contain high concentrations of vWF polypeptide in essentially insoluble form. Solubilization of vWF polypeptide was accomplished according to the following procedure. As explained in Example 2, p7E and pJD18 extracts responded very differently to solubilization procedures. See Maniatis, T. et al., *Molecular Cloning*, 2nd ed., vol. 3, Sec. 17.37, (1989) Cold Spring Harbor Laboratory Press, Cold Spring Harbor, NY, for a general discussion of the properties of, and successful manipulation strategies for, inclusion bodies.

The cells were harvested by centrifugation at 4000 g for 15 minutes in a JA-14 rotor at 4° C. The pelleted cells were washed in 50 ml of ice cold buffer (0.1M NaCl, 10 mM Tris pH 9.0, 1 mM EDTA) and repelleted by centrifugation at 4000 g at 4° C.

The cell pellets from p7E, p7D and pJD18 cultures were each redissolved in 5 ml of lysing buffer and kept ice-cold for 30 minutes. The lysing buffer comprises a solution of sucrose 25%(w/v), 1 mM phenylmethylsulfonylfluoride (PMSF), 1 mM ethylene diaminetetraacetic acid (EDTA), 2 mg/ml lysozyme and 50 mM Tris hydrochloride, adjusted to pH 8.0.

After the 30 minute incubation, aliquots of 1.0 Molar $MgCl_2$ and $MnCl_2$ were added to make the lysing solution 10 mM in each cation. Sixty μg of DNAseI (Boehringer-Mannheim) was then added and the incubation was continued at room temperature for 30 minutes.

Twenty ml of buffer No. 1 (0.2M NaCl, 2 mM EDTA, and 1% (w/v) 3-[(3-cholamidopropyl)-dimethylammonio]-1-propanesulfonate (CHAPS), 1% (w/v) Non-idet 40, and 20 mM Tris hydrochloride, pH 7.5) was then added to the incubation mixture. The insoluble material was pelleted by centrifugation at 14,000 g (12,000 rpm in a JA-20 rotor) for 30 minutes at 4° C.

The relatively insoluble pelleted material derived from each culture (which contains the desired polypeptides except in the case of p7D) was washed at 25° C. in 10 ml of buffer No. 2 (0.5% (w/v) Triton X-100 surfactant, 2 mM EDTA, 0.02M Tris hydrochloride, pH 7.5) and vortexed extensively. The suspension was centrifuged at 14,000 g for 30 minutes at 4° C. and the supernatant was then discarded. The process of resuspension of the pelleted material in buffer No. 2, vortexing and centrifugation was repeated twice.

Each pellet was then washed in 5 ml of buffer No. 3 (0.02M Tris hydrochloride, pH 7.5, and 2 mM EDTA) at 25° C. and vortexed extensively. The suspension was then centrifuged at 4° C. for 30 minutes at 14,000 g after which the supernatant was discarded leaving a pellet of inclusion body derived material (the "wet pellet") with a clay-like consistency (With respect to the following final steps, and in replacement therefor, see also Example 20 which presents an additional improved procedure).

The insoluble pellet was slowly redissolved in an 8 Molar urea solution held at room temperature for 2 hours, after which solubilization was continued overnight at 4° C. The urea-soluble material was extensively dialyzed against a solution of 0.15M NaCl containing 20 mM Hepes (N-[2-hydroxyethyl]piperazine-N-[2-ethanesulfonic acid]) (pH 7.4) ("Hepes-buffered saline") at 4° C.

The solublized peptide extracts were assayed for purity (Example 2), used in vWF binding inhibition assays (Example 3) or subject to further purification. Further purification steps should not be delayed and the samples should remain cold.

The cysteine-free vWF polypeptide (comprising subunit positions 441 to 733) constitutes more than 75% of the material solubilized from the inclusion bodies according to the above procedure. Further purification of the cysteine-free mutant vWF polypeptide was accomplished by redialyzing the partially purified peptide extract against 6M guanidine·HCl, 50 mM Tris·HCl, pH 8.8 followed by dialysis against 6M urea, 25 mM Tris·HCl, 20 mM KCl, 0.1 mM EDTA, pH 8.0. The extract was then subjected to high performance liquid chromatography using Q-Sepharoses® Fast Flow (Pharmacia, Uppsala, Sweden) for anion exchange. The column was preequilibrated with 6M urea, 25 mM Tris·HCl, 20 mM KCl, 0.1 mM EDTA pH 8.0. Elution of the vWF polypeptide utilized the same buffer except that the concentration of KCl was raised to 250 mM. Polypeptide samples used for further assays were redialyzed against 0.15M NaCl, 20 mM Hepes, pH 7.4. However, long term storage was best achieved in urea buffer (6M urea, 25 mM Tris·HCl, 20 mM KCl, 0.1 mM EDTA pH 8.0. Final p7E-vWF polypeptide percent amino acid compositions (by acid hydrolysis) compared closely with values predicted from published sequence information (Bonthron, D. et al. and also Mancuso, D. et al. in Example 1, supra; see also FIG. 1).

Example 2
Characterization of the cysteine-free mutant von Willebrand factor fragment produced by expression plasmid p7E Urea-solubilized and dialyzed polypeptides extracted from inclusion bodies of cultures containing expression plasmids p7E, p7D and pJD18 were analyzed using polyacrylamide gel electrophoresis (PAGE) and immunoblotting.

Characterization by SDS-Polyacrylamide Gel Electrophoresis

The purity and nature of the expression plasmid extracts, which had been urea-solubilized and then extensively dialyzed, were first analyzed using the denaturing sodium dodecylsulfate-polyacrylamide gel electrophoresis procedure of Weber, K. et al. *J. Biol. Chem.*, 244, 4406–4412 (1969), as modified by Laemli, U.K. *Nature*, 227, 680–685 (1970) using an acrylamide concentration of 10%. The resultant gels were stained with Coomassie blue and compared.

The extract from expression plasmid p7E contains as the major component, the mutant von Willebrand factor polypeptide which migrates with an apparent molecular weight of approximately 36,000 Daltons. The polypeptide appears as a single band under both reducing conditions (addition of between 10 and 100 mM dithiothreitol "DTT" to the sample for 5 min at 100° C. prior to running the gel in a buffer also containing the same DTT concentration) and nonreducing conditions, which result is consistent with the substitution of glycine residues for all of the cysteine residues therein. No vWF polypeptide could be extracted from host cells containing p7D expression plasmids as expected from the opposite orientation of the vWF cDNA insert.

The cysteine-containing vWF polypeptide expressed by host cells containing pJD18 plasmids, and which contains the wild type amino acid sequence of the 52/48 fragment, (herein represented by a residue 441 to 733 cloned fragment) behaved differently under reducing and nonreducing conditions of electrophoresis. The wild-type sequence expressed from pJD18 forms intermolecular disulfide bridges resulting in large molecular weight aggregates which are unable to enter the 10% acrylamide gels. After reduction (incubation with 100 mM DTT for 5 min at 100° C.), the vWF peptide migrates as a single band with a molecular weight of approximately 38,000.

Characterization by Immunoblotting

Polypeptides expressed from p7E, p7D and pJD18 were further characterized by immunoblotting ("Western blotting") according to a standard procedure Burnett et al., A. *Anal. Biochem.*, 112, 195–203, (1981) and as recommended by reagent suppliers. Samples containing approximately 10 μg of protein from the urea-solubilized and dialyzed inclusion body extracts of host cells (containing p7E, p7D and pJD18 plasmids) were subjected to electrophoresis on 10% polyacrylamide gels, Laemli, U.K. *Nature*, 227, 680–685 (1970), in the presence of 2% concentration of sodium dodecyl sulfate.

The proteins were blotted and immobilized onto a nitrocellulose sheet (Schleicher and Schuell, Keene, NH) and the pattern was then visualized using immunoreactivity.

The von Willebrand factor-specific monoclonal antibodies (from mice) used to identify the polypeptides were RG-46 (see Fugimura, Y. et al. *J. Biol. Chem.*, 261(1), 381–385 (1986), Fulcher, C.A. et al. *Proc. Natl. Acad. Sci.*

USA, 79, 1648–1652 (1982)), and NMC-4 (Shima, M. et al. J. Nara Med. Assoc., 36, 662–669 (1985)), both of which have epitopes within the expressed vWF polypeptide of this invention.

The secondary antibody ($^{125}$I-rabbit anti-mouse IgG), labelled by the method of Fraker, P.J. et al. *Biochem. Biophys. Res. Commun.*, 80, 849–857 (1978)), was incubated for 60 minutes at 25° C. on the nitrocellulose sheet. After rinsing, the sheet was developed by autoradiography.

Peptide extracts from host cells containing p7E and pJD18 expression plasmids display strong immunoreactivity for RG-46 antibody and a weaker but definite affinity for NMC-4 antibody. As expected, peptide extracts from p7D plasmids show no immunoreactivity with either RG-46 or NMC-4.

Example 3
Inhibition of Botrocetin-Induced Binding of vWF to Platelets by the Cysteine-Free Mutant Polypeptide Expressed by p7E It has been demonstrated that botrocetin, extracted from the venom of *Bothrops jararaca* modulates the in vitro binding of multimeric von Willebrand factor to platelets (Read, et al. *Proc. Natl. Acad. Sci.*, 75, 4514–4518 (1978)) and that botrocetin binds to vWF within the region thereof containing amino acid sequence positions 441–733 (of the mature subunit), and thus the GPIb binding domain. (Andrews, R.K. et al., *Biochemistry*, 28, 8317–8326 (1989)).

The urea-solubilized and dialyzed polypeptide extracts, obtained (according to the method of Example 1) from cultures containing expression plasmids p7E, p7D and pJD18, were tested without further purification for their ability to inhibit botrocetin-induced vWF binding to formalin-fixed platelets on a dose dependent basis.

Formalin-fixed platelets, prepared according to the method of MacFarlane, D. et al., *Thromb. Diath. Haemorrh.* 34, 306–308 (1975), were pre-incubated at room temperature for 15 minutes with specified dilutions of peptide extracts obtained from cultures containing pJD18, p7D, and p7E plasmids. Botrocetin, (Sigma, St. Louis, MO) to a final concentration of 0.4 μg/ml, and $^{125}$I-labelled multimeric vWF (isolated from human plasma cryoprecipitate according to the method of Fulcher, C.A. et al. *Proc. Natl. Acad. Sci. USA*, 79, 1648–1652 (1982), and labelled according to the method of Fraker, P.J. et al. *Biochem. Biophys. Res. Commun.*, 80, 849–857 (1978)) were then added to the incubation mixture, and the amount of $^{125}$I- vWF bound to the platelets was determined.

$^{125}$I-vWF binding to the platelets was referenced against 100% binding which was defined as the amount of $^{125}$I-vWF bound in the absence of added peptide extracts.

It was demonstrated that peptide extracts from expression plasmids p7D, and pJD18 (unreduced and unalkylated) cannot compete with plasma-derived vWF for platelet GPIb receptor binding sites. The peptide extract from plasmid p7E was effective in a dose dependent manner (using a range of 0 to 100 μg extract/ml) in inhibiting vWF binding. The concentration of urea-solubilized polypeptide extract (μg/ml) in the incubation mixture reflects the total protein concentration from the extract. Addition of peptide extracts to the reaction mixture causes certain nonspecific effects which raise apparent initial binding to 110% of the value found in the absence of the added peptide extracts. The $^{125}$-IvWF concentration used was 2 μg/ml.

Example 4
Expression of a Mutant vWF Fragment of Reduced Cysteine Content Containing a Disulfide-Dependant Conformation Utilizing the procedures of Example 1, except as modified below, a mutant vWF polypeptide fragment (corresponding to the mature vWF subunit sequence from residue 441 to residue 733) was prepared in which the cysteines at positions 459, 462, 464, 471 and 474 were each replaced by a glycine residue. Cysteine residues were retained at positions 509 and 695, and allowed to form an intrachain disulfide bond.

Site directed mutagenesis was performed only with oligonucleotides No. 459 and 471, thereby substituting glycine codons only at positions 459, 462, 464, 471 and 474. Upon completion of mutagenesis procedures, the sequence of the mutant vWF cDNA was confirmed using the single-stranded dideoxy method.

The double-stranded form of the vWF cDNA insert (containing 5 cysteine to glycine mutations) was then removed from M13mp18 phage by treatment with EcoRI and HindIII restriction endonucleases, modified as in Example 1 with BamHI linkers, and cloned into pET-3A. The pET-3A vehicle so formed is referred to as "p5E" or p5E expression plasmid.

The p5E expression plasmids were then cloned into ampicillin sensitive *E.coli* strain BL21(DE3), Novagen Co., Madison, WI, according to the procedure of Hanahan, D., *J. Mol. Biol.*, 166, 557–580 (1983). The p5E mutant polypeptide was expressed from cultures of *E.coli* BL21(DE3) following the procedure of Example 1 except that solubilization of inclusion body pellet material in the presence of 8 Molar urea need not be continued beyond the initial 2 hour period at room temperature, at which point redissolved material had reached a concentration of 200 μg/ml. Oxidation of cysteine residues 509 and 695 to form a disulfide bond was accomplished by dialysis overnight against Hepes-buffered saline. Formation of intrachain rather than interchain disulfide bonds is favored by allowing thiol oxidation to proceed at a low protein concentration such as 50–100 μg/ml.

As in Example 1 pertaining to the p7E extracts, final purification of urea-solubilized inclusion body preparations was accomplished by dialysis against the 6M guanidine and 6M urea buffers followed by anion exchange chromatography.

Example 5
Characterization of the Mutant vWF Fragment Produced by Expression Plasmid p5E The mutant von Willebrand factor polypeptides produced by cultures containing expression plasmid p5E were characterized utilizing the procedures of Example 2, and in particular compared with the vWF fragment expressed by plasmid p7E.

Urea-solubilized and dialyzed polypeptides extracted from inclusion bodies (according to the procedure of Example 4) were compared with similar extracts from p7E plasmid cultures produced as in Example 1.
Characterization by SDS-Polyacrylamide Gel Electrophoresis The denaturing sodium dodecylsulfate gel procedure of Example 2 was used to compare the p5E vWF fragments, which can form disulfide bonds using cysteine residues 509 and 695, with the p7E fragment which has no cysteine residues. Electrophoresis was conducted using 7.5 μg of protein extract per lane on 10% acrylamide gels under reducing (100 mM dithiothreitol) and nonreducing conditions.

Under reducing conditions, and after staining with Coomassie blue, extracts from p7E and p5E have identical electrophoretic mobilities.

Electrophoresis under nonreducing conditions, however, demonstrates the effects of disulfide bonds involving residues 509 and 695. A substantial amount of the p5E extract appears as a high molecular weight complex (resulting from interchain disulfide bonds) which enters the gel only slightly. Densitometric scanning of the gels of initial preparations indicates that approximately 25% of the p5E polypeptide material found on nonreducing gels is represented by monomers of the 441–733 fragment having an apparent molecular weight of approximately 38,000. The percent of monomer present in p5E extracts can be improved significantly by conducting urea solubilization, dialysis, and thiol oxidation at a more dilute protein concentration, such as 50–100 $\mu$g/ml, to favor intrachain rather than interchain disulfide bond formation.

This p5E monomeric species has a slightly higher mobility during electrophoresis under nonreducing conditions than the comparable p7E product species which has no cysteine residues. The mobilities of these p5E and p7E monomeric 38 kDa species appear identical under reducing conditions. The slightly accelerated mobility of a polypeptide which retains tertiary structure in the presence of SDS under nonreducing conditions, when compared to the mobility of the homologous polypeptide which the anionic detergent converts completely into a negatively charged fully rigid rod under said conditions, is generally considered suggestive of the presence of an intrachain disulfide bond.

Characterization by Immunoblotting

The behavior of p5E and p7E extracts were also examined using immunological methods.

As in Example 2, vWF-specific murine monoclonal antibodies RG-46 and NMC-4 were used as probes. RG-46 has been demonstrated to recognize as its epitope a linear sequence of amino acids, comprising residues 694 to 708, within the mature von Willebrand factor subunit. The binding of this antibody to its determinant is essentially conformation independent. Mohri, H. et al., *J. Biol. Chem.*, 263 (34), 17901–17904 (1988).

NMC-4 however, has as its epitope the domain of the von Willebrand factor subunit which contains the glycoprotein Ib binding site. Mapping of the epitope has demonstrated that it is contained within two discontinuous domains (comprising approximately mature vWF subunit residues 474 to 488 and also approximately residues 694 to 708) brought into disulfide-dependent association, Mohri, H. et al., supra, although it was unknown whether the disulfide bond conferring this tertiary conformation in the native vWF molecule was intrachain or interchain. Id. at 17903.

7.5 $\mu$g samples (of protein) were first run on 10% SDS polyacrylamide gels so that the antigenic behavior of particular bands (under reducing and nonreducing conditions) could be compared with results obtained above by Coomassie blue staining. Immunoblotting was performed as in Example 2 to compare p5E and p7E extracts.

Application of antibody to the nitrocellulose sheets was usually accomplished with antibody solutions prepared as follows. Mice were injected with B-lymphocyte hybridomas producing NMC-4 or RG-46. Ascites fluid from peritoneal tumors was collected and typically contained approximately 5 mg/ml of monoclonal antibody. The ascites fluid was mixed (1 part per 1000) into blocking fluid (PBS containing 5% (w/v) non-fat dry milk, Carnation) to minimize non-specific background binding. The antibody-containing blocking fluid was then applied to the nitrocellulose.

Under nonreducing conditions, the single chain p5E polypeptide fragment (representing the sequence from residue 441 to residue 733) displayed an approximate 120 fold increase in binding affinity for NMC-4 compared to the comparable cystein-free species isolated from p7E also representing the primary sequence from residue 441 to 733. After electrophoresis under reducing conditions (utilizing 100 mM DTT), the single chain p5E species showed a remarkably decreased affinity for NMC-4, which was then very similar to that of the cysteine-free p7E species under either reduced or nonreduced conditions. NMC-4 also fails, under reducing or non-reducing conditions, to recognize as an epitope disulfide-linked dimers from the p5E extract.

The nitrocellulose filters used to produce autoradiographs based on NMC-4 were rescreened with RG-46 by subtracting the initial NMC-4 exposure response, which was kept low through a combination of low antibody titer and short exposure time. The binding of RG-46 to the p7E 36,000 kDa polypeptide on the filters is the same whether reducing or non-reducing conditions were chosen, consistent with the replacement of all cysteines by glycine in the expressed polypeptide.

A large molecular weight vWF antigen (reactive to RG-46) is present in the p5E polypeptide extract under nonreducing conditions. These p5E vWF aggregates (reflecting interchain disulfide bonds) migrate under reducing conditions in the same position as the p7E polypeptide indicating disruption of their disulfide contacts. However, the large p5E interchain disulfide aggregates which are readily recognized under nonreducing conditions by RG-46 are not recognized by NMC-4 under either reducing or nonreducing conditions. It is thus demonstrated that the disulfide bond between residues 509 and 695 in native multimeric vWF subunits represents an intrachain contact.

Example 6

Inhibition of the Binding of an Anti-GPIb Monoclonal Antibody by p5E Polypeptide Monoclonal antibody LJ-Ib1 is known to completely inhibit von Willebrand factor-platelet glycoprotein Ib interaction. Handa, M. et al., *J. Biol. Chem.*, 261(27), 12579–12585 (1986). It reacts specifically with the amino terminal 45 kDa domain of GPIb$\alpha$ which contains the vWF binding site. Vicente, V. et al., *J. Biol. Chem.*, 265, 274–280 (1990).

To assess the inhibitory activity of p5E extracts on antibody binding, a concentration of LJ-Ib1 was first selected which would, in the absence of p5E extracts, provide half-maximal binding.

LJ-Ib1 was iodinated by the procedure of Fraker, D.J. et al., *Biochem. Biophys. Res. Commun.*, 80, 849–857 (1978) using $I^{125}$ from Amersham, Arlington Heights, IL and Iodogen (Pierce Chemical Co., Rockford, IL). Washed platelets were prepared by the albumin density gradient technique of Walsh, et al., *Br. J. Haematol.*, 36, 281–298 (1977), and used at a count of 1 x $10^8$ /ml. Half-maximal binding of antibody to platelets was observed at 10 $\mu$g/ml LJ-Ib1 concentration, which concentration was selected for p5E polypeptide inhibition studies.

The p5E polypeptide extract was purified according to the procedure of Example 4 including final purification of the urea-solubilized inclusion body preparation by dialysis against 6.0M guanidine and urea solutions followed by Q-Sepharose® chromatography.

Figure 3B:
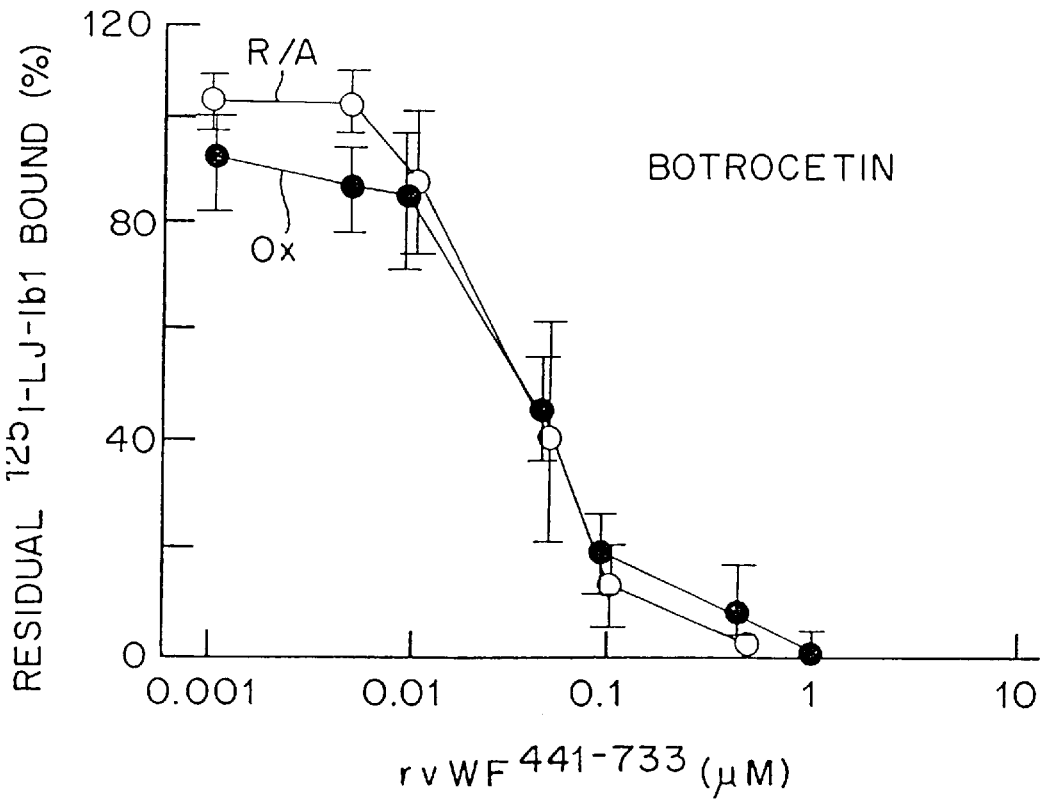

To evaluate binding, platelets were incubated for 30 minutes at 22–25° C. with LJ-Ib1 (10 $\mu$g/ml) and concentrations of purified p5E protein (.002–10.0 $\mu$Molar) as indicated in FIGS. 3A and 3B. Inhibition was plotted in the presence of 2 $\mu$g/ml botrocetin, Sigma Chemical Co., St. Louis, MO, (FIG. 3B) and in the absence of botrocetin (FIG. 3A).

Less than 5 percent of the $^{125}$I label bound to the platelets was contributed by labelled substances other than LJ-Ib1 as determined by binding competition experiments in the presence of a 100 fold excess of unlabelled LJ-Ib1. Background labelling was subtracted from data points. Binding of $^{125}$I LJ-Ib1 was expressed as a percentage of a control assay lacking recombinant polypeptides. Fifty percent inhibition of $^{125}$I LJ-Ib1 binding to platelets was achieved at 10 μM of p5E polypeptide without botrocetin whereas in the presence of botrocetin (2 μg/ml), 50% inhibition may be achieved at less than 0.1 μM. It is known that botrocetin induces in circulating multisubunit von Willebrand factor and single subunits thereof a conformational change which enhances or permits binding to the GPIbα receptor. This example demonstrates that the p5E polypeptide (containing an intrachain cysteine 509–695 bond) behaves very much like native circulating von Willebrand factor with respect to how its activity is modulated by botrocetin. Structural similarity is therefore indicated.

Example 7
Expression of Homodimeric 116 kDa von Willebrand Factor Fragment in Stable Mammalian Transformants This example is illustrative of conditions under which a DNA sequence encoding the mature vWF subunit fragment having an amino terminus at residue 441 (arginine) and a carboxy terminus at residue 730 (asparagine) may be expressed, and of the secretion from cultured mammalian host cells of a glycosylated homodimeric form of the 441–730 vWF fragment having native tertiary structure.

Expression of the 116 kDa homodimer is achieved using a DNA construct in which the following structural elements are assembled in a 5' to 3' direction (referring to the coding or nontranscribed strand):

(A) a eucaryotic consensus translation initiation sequence, CCACC; and (B) the initiating vWF methionine codon followed by the remaining 21 amino acids of the vWF signal peptide; and (C) the coding sequence corresponding to the first three amino acids from the amino terminus region of the vWF propeptide; and (D) the coding sequence for vWF amino acid residues 441–730; and (E) the "TGA" translation termination codon.

The cDNA clone, pvWF, encoding the entire pre-pro-vWF gene was obtained from Dr. Dennis Lynch, Dana-Farber Cancer Institute, Boston, MA and was prepared as described in Lynch, D.C. et al., *Cell*, 41, 49–56 (1985). Preparation of pvWF was described in Example 1.

Detailed procedures necessary for the expression of the homodimeric Arg$^{441}$ to Asn$^{730}$ fragment of mature vWF subunit from mammalian host cells are described in the publication Azuma, H. et al., Independent Assembly and Secretion of a Dimeric Adhesive Domain of von Willebrand Factor Containing the Glycoprotein Ib-Binding Site, *J. Biol. Chem.*, 266(19), 12342–12347 (1991). It should be noted that this recombinantly produced molecule intrinsically self-assembles through intermolecular disulfide bond formation into a dimer (116 kDa) of the 52/48 kDa residue 441–730 polypeptide domain, duplicating its role in the final structure of vWF as isolated from the blood.

Production of monomeric residue 441–730 polypeptides requires inactivation, deletion or replacement of one or more of cysteine residues 459, 462 and 464 thereof (the interchain disulfide contacts). This may be accomplished effectively using site-directed mutagenesis of the vWF construct when contained in an appropriate cloning vehicle, such as M13mp18, as described below.

Example 8
Construction of a Mammalian Transformant for the Expression of the Monomeric 441–730 Mature von Willebrand Factor Subunit Fragment with Cysteine-to-Glycine Mutations at Residues 459. 462 and 464

This example is illustrative of conditions under which a DNA sequence encoding a mature vWF subunit fragment, which has an amino terminus at residue 441 (arginine) and a carboxy terminus at residue 730 (asparagine) and which further contains glycine residues substituted for cysteine residues at positions 459, 462 and 464 thereof, can be constructed and transfected into mammalian cells.

The SalI-XbaI insert of pAD3-2 (see Example 7) was removed by restriction and then cloned into pcDNA1 vector (Invitrogen, San Diego, CA) which had been previously digested with XhoI and XbaI restriction enzymes. Since XhoI and SalI restriction sites contain identical internal sequences -TCGA- / -AGCT- , a SalI restricted fragment may be annealed into an XhoI site. The fragments were ligated with T$_4$ DNA ligase; however the integrity of the XhoI site was not restored. This plasmid construct was designated pAD4/WT.

Site-Directed Mutagenesis Using M13mp18 pAD4/WT was restricted with EcoRI and SmaI enzymes. pcDNA1 vector contains an EcoRI site within its polylinker region which is upstream from the XhoI ("SalI") site but contains no SmaI site. As shown in FIG. 1B (SEQ ID NO: 1), a unique SmaI site (CCCGGG) is contained within the vWF cDNA insert, spanning mature subunit residues 716 (glycine) to residue 718 (glycine).

Accordingly, an approximate 950 base pair EcoRI-SmaI fragment of pAD4/WT was subcloned into the EcoRI-SmaI site within the polylinker region of M13mp18 phage. The vWF sequence in M13mp18 was then mutagenized and reinserted into the previously restricted pAD4/WT construct leading to reassembly of the intact residue 441–730 vWF sequence.

The mutagenesis followed the procedure of Example 1 and Kunkel, T.A., supra, and utilized the following oligonucleotide.

Oligonucleotide(7) - see SEQ ID NO: 8
3' - GGACTCGTGCCGGTCTAACCACTACAACAG - 5'
5' - cctgagcacggccagattggccacggtgatgttgtc - 3'
         Gly$_{459}$   Gly$_{462}$Gly$_{464}$ The hybridizing oligonucleotide is shown (3'→5') in capital letters and is equivalent to transcribed strand (non-coding strand DNA). Underlined letters indicate the single base mutations for the mutant codons. The equivalent coding strand is shown in lower case letters with the corresponding glycine substitutions identified by three letter designation.

The mutant 950 base pair EcoRI-SmaI fragment was then re-inserted into the EcoRI-SmaI site of the previously restricted pAD4/WT plasmid. The mutant construct was designated pAD4/Δ3C. To facilitate longterm storage and propagation, pAD4/Δ3C was transformed into ampicillin sensitive *E.coli* strain XS-127 according to the method of Hanahan, D., *J. Mol. Biol.*, 166, 557–580 (1983).

Consistent with the procedures of Example 1, the sequence of the mutant cDNA was confirmed by the dideoxy method and the plasmid was purified by CsCl/ethidium bromide equilibrium centrifugation.

Transformation of COS-1 Cells PAD4/Δ3C was introduced into COS-1 cells (SV 40 transformed African Green monkey kidney cells, ATCC-CRL 1650) by a standard calcium phosphate-mediated transfection procedure. Chen, C. et al., *Mol. Cell. Biol.,* 7(8), 2745–2752 (1987).

COS-1 cells were grown at 37° C. in Dulbecco's modified Eagle's medium (DMEM) (Gibco/Life Technologies, Inc., Gaithersburg, MD) supplemented with 10% fetal calf serum (FCS) under a 5% $CO_2$ atmosphere, and then subcultured 24 hours prior to transformation at a density of 1.5 x $10^5$ cells/60 mm tissue culture dish (approximately 25% of confluence). COS-1 cells have a doubling time in DMEM/10% FCS of approximately 20 hours under these conditions.

To accomplish transformation, pAD4/Δ3C plasmids were recovered from cultures of *E.coli* strain XS-127 according to the method of Birnboim, H.C. and Doly, J., *Nucleic Acids Research,* 7, 1513 (1979). Ten μg of plasmids were applied to the cells of each 60 mm dish in a calcium phosphate solution according to the method of Chen et al., supra. After inoculation with plasmid, the cells were maintained in DMEM/10% FCS for 8 hours at 37° C. in a 5% $CO_2$ atmosphere.

The growth medium was then replaced with a solution of phosphate-buffered saline/10% (v/v) glycerol. The cultures were then maintained in glycerol-PBS for 2 minutes to facilitate the production of transformants (Ausukel, et al. eds, *Current Protocols in Molecular Biology,* p.9.1.3, Wiley & Sons (1987)). After 2 minutes, the glycerol-PBS solution was replaced with DMEM/10% FCS. Antibiotic resistance was not used to select for stable transformants. The cells were then maintained at 37° C. in DMEM/10% FCS in a 5% $CO_2$ atmosphere.

Example 9
Transformation of COS-1 Cells by DAD4/WT plasmids

COS-1 cells were also transformed successfully with pAD4/WT plasmids. Although antibiotic resistance was not used to select for stable transformants, transient expression of the 116 kDa fragment therefrom was particularly useful for the purpose of comparing the properties of the 116 kDa mutagenized polypeptide produced by pAD4/Δ3C plasmids to those of the pAD4/WT 116 kDa homodimer.

Following the procedures of Example 9, pAD4/WT plasmids were recovered from storage cultures of *E.coli* strain XS-127. Transformation of COS-1 cells with pAD4/WT was then accomplished using the procedures of Example 8. The cells were then maintained at 37° C. in DMEM/10% FCS in a 5% $CO_2$ atmosphere.

Example 10
Construction of Mammalian Transformants Which Express Mutant 441–730 Mature von Willebrand Factor Subunit Fragments Wherein Each Mutant Contains a Single Cysteine-to-Glycine Substitution Following the procedures of Example 8, and using suitable oligonucleotides for site-directed mutagenesis, three plasmids (pAD4/$G^{459}$, pAD4/$G^{462}$ and pAD4/$G^{464}$, collectively referred to as "pAD4/Δ1C plasmids") were constructed. Such plasmids are identical to pAD4/WT except that each contains a single base pair mutation which corresponds to a single cysteine to glycine substitution at mature vWF subunit residue positions 459, 462 and 464 respectively. The oligonucleotides used are identical to oligonucleotide (7) used to prepare pAD4/Δ3C except that each contains only one of the three mutant codons of that oligonucleotide, the other two codons being represented by the wild type coding sequence. To facilitate longterm storage and propagation, samples of pAD4/$G^{459}$, pAD4/$G^{462}$, and pAD4/$G^{464}$ were each cloned into ampicillin sensitive *E.coli* strain XS-127 following the method of Example 8.

Consistent with the procedures of Example 8, the sequences of the mutant cDNAs were confirmed by the dideoxy method and the plasmids were purified by CsCl/ethidium bromide equilibrium centrifugation.

Transformation of COS-1 cells with either pAD4/$G^{459}$, pAD4/$G^{462}$ or pAD4/$G^{464}$ plasmids was accomplished according to the protocol of Example 8. Antibiotic resistance was not used to select for stable transformants. The cells were then maintained at 37° C. in DMEM/10% FCS in a 5% $CO_2$ atmosphere.

Example 11
Expression and Characterization of von Willebrand Factor Subunit Fragments by COS-1 Cells Transformed with pAD4/WT and PAD4/Δ3C plasmids COS-1 cells which had been transformed with pAD4/Δ3C or pAD4/WT plasmids according to the procedures of Examples 8 and 9 respectively were cultured to express the encoded vWF DNA as explained below. COS-1 cells similarly transformed with pcDNA1 plasmid vector (not containing a vWF cDNA insert) were used as controls.

COS-1 cells at a density of 4–5×$10^5$/60 mm dish were transformed by adding, at time zero, 10 μg of pAD4/WT, pAD4/Δ3C or pcDNA1 plasmid. Following the procedure of Examples 9 and 10, the cells were glycerol-shocked after a period of 8 hours. The cells were then covered with DMEM/10% FCS at 37° C. in a 5% $CO_2$ atmosphere for 32 hours.

The cells for each culture were then rinsed three times with PBS and the incubation was continued with DMEM (without FCS) which was supplemented with $^{35}$S-methionine (Amersham Co., Arlington Heights, IL) having a specific activity of 1000 Ci/mmol to a final concentration of 100 μCi/ml. The cells were returned to the incubator for 16 hours, after which time the respective culture media were harvested for purification by immunoprecipitation of secreted vWF polypeptides.

Immunoprecipitation followed generally the procedure of Example 7. Five ml volumes of culture media were incubated with 0.5 ml of 10X immunoprecipitation buffer, 0.05 mg of NMC-4 antibody and 0.05 mg of RG-46 antibody for 16 hours.

Treatment with protein A-Sepharose®4B was performed according to Example 7. Samples of IgG-complexed vWF protein were dissociated prior to SDS-PAGE in SDS-containing sample buffer.

For analysis of the vWF polypeptides under reducing conditions, the sample buffer was modified to contain 100 mM dithiothreitol (DTT).

Results

The gels were run under reducing and non-reducing conditions and were dried and subject to autoradiography to develop the $^{35}$S label. No $^{35}$S-labelled protein was detected as an immunoprecipitate derived from control cultures of COS-1 cells (transformed by unmodified pcDNA1 vehicle) under either reducing or non-reducing conditions (see gel lanes designated MOCK).

COS-1 cells transformed with pAD4/WT plasmids produce, under non-reducing conditions, a prominent $^{35}$S-labelled band of an approximate apparent molecular weight of 116,000. This value is consistent with proper mammalian glycosylation of the 441–730 fragment. When run under reducing conditions, no 116 kDa material is apparent, consistent with the reduction of the disulfide bonds which stabilize the 116 kDa homodimer. Under reducing conditions, a prominent $^{35}$S-labelled band is visualized of approximately 52,000 apparent molecular weight. The apparent 52 kDa value is again consistent with proper glycosylation of the reduced monomeric 441–730 fragment.

The gel lanes corresponding to transformation with pAD4/Δ3C show no apparent 116 kDa material. Instead a band is apparent, under reducing and non-reducing conditions, at an apparent molecular weight of approximately 52,000.

Thus, mutagenesis to replace cysteine residues 459, 462 and 464 within the 441–730 vWF fragment with glycine residues results in the successful expression of a non-dimerizing polypeptide presumably having only intrachain (471 to 474 and 509 to 695) disulfide bonds. Interaction with NMC-4 (see also Example 7) is known to require an intact 509 to 695 intrachain disulfide bond, thereby demonstrating the presence of native wild type tertiary structure in the polypeptide produced by pAD4/Δ3C.

The gels also demonstrated the presence of low molecular weight $^{35}$S-labelled material (under reducing and non-reducing conditions) probably indicating that not all vWF polypeptides produced by pAD4/WT constructs successfully dimerize and that proteolysis and/or incomplete glycosylation of the polypeptide may prevent higher yields. Proteolysis and/or incomplete glycosylation also presumably affect the yield of the monomeric vWF polypeptide produced by the pAD4/Δ3C transformants. Some high molecular weight aggregate material (essentially not entering the gels) is present in non-reduced samples from pAD4/WT and pAD4/Δ3C.

Example 12
Use of NMC-4 Monoclonal Antibody to Immunoprecipitate vWF Polypeptides Secreted by pAD4/WT and pAD4/Δ3C transformed COS-1 cells The NMC-4 monoclonal antibody has as its epitope the domain of the von Willebrand factor subunit which contains the glycoprotein Ib binding site. Mapping of the epitope has demonstrated that it is contained within two discontinuous domains (comprising approximately mature vWF subunit residues 474 to 488 and also approximately residues 694 to 708) brought into disulfide-dependent association by an intrachain (residues 509 to 695) disulfide bond.

Thus, reactivity with NMC-4 is important evidence of whether a particular recombinant 441–730 mature vWF subunit fragment has assumed the tertiary structure of the analogous wild type residue 441–730 domain.

Accordingly, the procedure of Example 11 was followed to characterize vWF polypeptides secreted by pAD4/WT and pAD4/Δ3C transformed COS-1 cells, with the modification that immunoprecipitation of the culture media was effected solely with NMC-4 antibody (0.05 mg NMC-4 per 5 ml of culture media to which 0.5 ml of 10X immunoprecipitation buffer had been added).

Samples were run under reducing and non-reducing conditions. Consistent with the results of Example 11, the major component isolated from pAD4/WT culture medium has an apparent molecular weight of 116 kDa under non-reducing conditions and 52 kDa under reducing conditions.

Although only a small fraction of the total pAD4/Δ3C derived vWF polypeptide material binds to NMC4 (compared to conformation independent RG-46), a band of apparent molecular weight of 52 kDa is visible under reducing and non-reducing conditions in gels of NMC-4 immunoprecipitates.

Example 13
Expression and Characterization of von Willebrand Factor Subunit Fragments Produced by COS-1 Cells Transformed with pAD4/G$^{459}$, pAD4/G$^{462}$ or pAD4/G$^{464}$ plasmids Transformation of COS-1 cells by either pAD4/G$^{459}$, pAD4/G$^{462}$ or pAD4/G$^{464}$ plasmid (collectively the "pAD4/Δ1C plasmids") was accomplished according to the procedure of Example 10. Culture media were analyzed for secreted vWF polypeptide according to the procedure of Example 7, using only NMC-4 for immunoprecipitation.

$^{35}$S-labelled proteins, prepared according to Example 11, were immunoprecipitated by NMC-4 and run in SDS-polyacrylamide gels under reducing and non-reducing conditions and compared with vWF antigen produced by pAD4/WT and pAD4/Δ3C transformants.

The gels demonstrated that substitution of any one of the 3 cysteines (459, 462, 464) believed responsible for interchain disulfide contacts in native mature subunits prevents the formation of the homodimeric 116 kDA polypeptide characteristic of pAD4/WT transformed COS-1 cells. These three vWF antigens with a single glycine substitution appear predominantly as monomeric polypeptides of an apparent molecular weight of 52,000 under reducing or non-reducing conditions. That the predominant material has an apparent molecular weight of 52 kDa is strongly suggestive of correct glycosylation by the COS-1 cell transformants duplicating glycosylation seen in the human 52/48 kDa tryptic vWF fragment. Some inadequately glycosylated and/or proteolyzed vWF antigen (molecular weight less than 52 kDa) is also apparent in the gels. The relatively small fraction of pAD4/Δ3C vWF polypeptide which is successfully folded and secreted, thereby presenting an NMC-4 epitope, was shown by the low intensity of the pAD4/Δ3C transformant autoradiograph band of apparent 52,000 molecular weight.

Example 14
Preparation of Subsets of the 52/48 kDa Polypeptide

This example is illustrative of the preparation of polypeptides representing embodiments of the invention which are cysteine-deficient subsets derived from the residue 441–733 fragment of vWF subunit. The example is illustrative of conditions under which such subsets may be expressed from recombinant bacterial host cells. The subsets may be expressed also from recombinant eucaryotic cells, for example, by following the general procedures of Examples 7 and 8. The subsets are capable of interfering with the interaction of multimeric vWF and platelet GPIbα, that is, they have utility as antithrombotics.

There follows hereafter a description of the preparation of three groups of polypeptides comprising the aforementioned type subsets, with the first group of subsets being cysteine-free and those of the second and third groups of subsets having but two cysteine residues (five of the cysteine residues having been removed). The subsets of the second and third groups differ in that there is retained either the N-terminal region (second group) or the C-terminal region (third group) of the polypeptide.

Polypeptide Subsets (Cysteine-Free) of the Residue 441–733 Domain of vWF Subunit Mutant (fusion) polypeptides consisting of the residue 441–733 sequence, but lacking either the internal G10 (residues 474–488) or D5 (residues 694–708) region, were created using loopout mutagenesis in M13mp18 phage of restriction fragments of p7E constructs and then tested for antithrombotic activity.

Specifically, p7E plasmids were recovered from cultures of *E.coli* BL21(DE3) using an alkaline cell lysis procedure, Birnboim, H.C. and Doly, J., *Nucleic Acids Research*, 7, 1513 (1979) followed by purification by CsCl/ethidium bromide equilibrium centrifugation. An XbaI restriction site exists in p7E plasmid (contributed by the parent pET-3A vector) upstream from the T7 transcription promoter. Accordingly, the vWF insert (for residues 441–733) was removed as an XbaI-HindIII restriction fragment for loopout mutagenesis (see Example 1) in M13mp18 phage. Loopout of the G10 region or D5 region, respectively, was accomplished using the following oligonucleotides which represent non-coding strand (transcribed strand) DNA. Shown below the two 3'→5' oligonucleotides are the corresponding coding strands and resultant amino acid sequences.

Oligonucleotide (8) - see SEQ ID NO: 9
3' - GAG TGG CCA CTT CGG CAC TCG GGG TGG TGA - 5'
5' - ctc acc ggt gaa gcc gtg agc ccc acc act - 3'
    Leu Thr Gly Glu Ala Val Ser Pro Thr Thr
    469 470 471 472 473 489 490 491 492 493
                      ↑
       deletion of G10 binding peptide Oligonucleotide (9) - see SEQ ID NO: 10
3' - CTC TAG CAA TCG ATG CTG TAC CGT GTT CAG - 5'
5' - gag atc gtt agc tac gac atg gca caa gtc - 3'
    Glu Ile Val Ser Tyr Asp Met Ala Gln Val
    689 690 691 692 693 709 710 711 712 713
                      ↑
       deletion of D5 binding peptide DNA sequence analysis was used to confirm that the intended vWF coding sequences were produced. The two mutagenized XbaI-HindIII restriction fragments were then inserted into separate pET-3A plasmids that had been cut with XbaI and HindIII restriction endonuclease and which were thereafter designated p7E/ΔG10 and p7E/ΔD5.

The resultant mutant (fusion) vWF polypeptides were then tested for their ability to bind to GPIbα. Using the assay procedure of Example 6 (inhibition of the binding of LJ-Ib1 antibody to GPIbα in the absence of botrocetin modulator), it was determined that the residue 441–733 fragment, which was expressed from p7E and from which the "G10" peptide sequence was deleted, binds GPIbα. The p7E-derived fusion fragment lacking the "D5" peptide sequence did not. However, when the experiments were repeated using botrocetin as a modulator of binding (see the method of Example 6), both of the fused subfragments were effective in inhibiting binding by LJ-Ib1, and hence have antithrombotic utility.

Other in vitro assays which can be used to identify vWF-derived polypeptides having antithrombotic activity include inhibition of botrocetin-induced binding of vWF to platelets by the mutant polypeptide (see Example 3), and the inhibition of human platelet agglutination in a system using bovine vWF, but without a modulator such as botrocetin or ristocetin.

Cysteine-Deficient Polypeptide Subsets Having N-terminal Deletions

Therapeutic polypeptide subsets effective as antithrombotics have also been prepared which are patterned upon the residue 441–733 vWF subunit fragment, but which contain N-terminal deletions.

Preparation of such polypeptides was accomplished using loopout mutagenesis in M13mp18 phage of the XbaI-HindIII restriction fragment from p5E expression plasmid. Thus, the vWF encoding sequence (p5E) encoded cysteine for residue positions 509 and 695 and glycine at residue positions 459, 462, 464, 471 and 474. p7E sequence is also useful for expression of such antithrombotic polypeptides. Antithrombotic polypeptides equivalent to those expressed from p7E constructs can be made by reduction and alkylation of cysteine residues otherwise contained therein.

The design of oligonucleotides used to create N-terminal deletions in the vWF subunit fragment made reference to DNA sequence of the pET-3A vector that is upstream (5') from the codon encoding vWF residue 441. Expression of the residue 441–733 fragment as an EcoRI-HindIII insert (with both 5' and 3' ends thereof modified by BamHI linkers, Example 1) in pET-3A involves expression also of a twenty residue amino acid sequence (SEQ ID NO:11) that remains attached to the amino terminal of the vWF fragment. This sequence, as shown below, is encoded by vector DNA downstream from the T7 promoter site but does not affect adversely the therapeutic activity of the vWF polypeptide.

initiation codon
       ↓
    Met Ala Ser Met Thr Gly Gly Gln Gln Met
    Gly Arg Gly Ser Pro Gly Leu Gln Glu Phe Arg$_{441}$
                            ↑
                      from EcoRI It is noted that the EcoRI encoding sequence (Glu-Phe) survived modification with a BamHI linker in the $T_4$-DNA ligase procedure (Example 1) in this particular case. The corresponding pET-3A vector coding sequence located upstream from the initiating methionine and residue 441 (arginine) is as follows.

Oligonucleotide (11) - see SEQ ID NO: 12
5' - GAA GGA GAT ATA CAT ATG GCT AGC . . .
                       Met Ala Ser Accordingly, generation of N-terminal deletions was accomplished using loopout mutagenesis with a hybridizing oligonucleotide which encodes sequence from the vector (ending at the initiating methionine) and then the intended N-terminal region of the new vWF polypeptide.

Representative of the oligonucleotides necessary for the preparation of the therapeutic polypeptides is oligonucleotide 12 (SEQ ID NO: 13) which corresponds to non-coding strand (transcribed strand) DNA. Shown below this oligonucleotide are the corresponding coding strand and resultant amino acids.

3' - CCT CTA TAT GTA TAC GTC CTC GGC CCT CCG - 5'
    gga gat ata cat atg cag gag ccg gga ggc
              Met Gln Glu Pro Gly Gly
         474' 475 476 477 478 479

Representative of cysteine-deficient polypeptides reflecting such N-terminal deletions are Met·Gln$^{475}$ to Val$^{733}$, Met·Thr$^{492}$ to Val$^{733}$, and Met·Tyr$^{508}$ to Val$^{733}$. Such polypeptides (and other species having terminal deletion of any subsets of the vWF residue 441–508 sequence that contain one or more cysteine residues) have antithrombotic therapeutic activity. These polypeptides can present also the cysteine 509–695 loop when expressed from p5E constructs. Sequencing experiments have not been performed to determine if the bacterial expression system causes cleavage from the resultant polypeptides of the initiating methionine residue.

Cysteine-deficient Polypeptide Subsets Having C-Terminal Deletions

The procedure used to express recombinant bacterial polypeptides using pET-3A vectors results in polypeptides that comprise also a series of amino acids on the C-terminal side of Val$^{733}$, the additional residues arising from translation of vector sequence (see SEQ ID NO: 14).

Specifically, residue 441–733 fragments expressed from p5E (or p7E) constructs contain also 22 residues fused to the C-terminal side of residue 733 (valine) resulting from the expression of vector sequence prior to the first vector stop codon.

This pET-3A vector sequence, which reflects also modification (Example 1) of the HindIII site of the EcoRI-HindIII fragment by a BamHI linker, is (SEQ ID NO: 14):

Val Ser Ser Asp Pro Ala Ala Asn Lys Ala
733
Arg Lys Glu Ala Glu Leu Ala Ala Ala Thr
Ala Glu Gln *
       ↑
  stop codon In order to prepare an appropriate encoding DNA sequence for vWF polypeptides having C-terminal deletions, loopout mutagenesis was performed in p5E using hybridizing oligonucleotides patterned on noncoding strand DNA. To prepare a polypeptide (using the polypeptide ending at residue Asp$^{709}$ as an example), a hybridizing oligonucleotide was created encoding vWF subunit sequence (for example, from residue 706 to 713) that included also between certain codons thereof (for example, codon 709 and codon 710) the stop codon/reading frame shift sequence 3' - ACT·ACT·T - 5'.

Accordingly, vWF-derived polypeptides were generated that have C-terminal deletions and which terminate at residues 709, 704, 700 and 696 respectively.

Cysteine-deficient Polypeptide Subsets Having N-terminal and C-terminal Deletions Therapeutic polypeptide subsets effective as antithrombotics have also been prepared which are patterned upon the residue 441–733 vWF subunit fragment, but which contain both N-terminal and C-terminal deletions therefrom.

Preparation of two such polypeptides (Met·Tyr$^{508}$ to Pro$^{704}$ and also Met·Tyr$^{508}$ to Asp$^{696}$) followed the procedure discussed above for the making of N-terminal deletions (preparation of Met·Tyr$^{508}$ to Val$^{733}$) followed by the above-described strategy to establish C-terminal deletions therefrom. Specifically, hybridizing oligonucleotides for loopout mutagenesis in M13mp18 were selected to insert the above-mentioned stop codon/reading frame shift sequence between residues 704 and 705 and between residues 696 and 697, respectively.

Example 15
Interaction of vWF Domains with GPIbα

To determine the structural requirements necessary to support binding of multimeric vWF to platelet GPIbα, a series of recombinant polypeptides comprising one or more domains of amino acid sequence produced (Example 14) from the recombinant vWF residue 441–733 fragment ("rvWF$^{441-733}$") were prepared. The sequences of the resulting polypeptides (deletion fragments) of rvWF are shown in FIG. 2. These polypeptides (hereinafter "domains") contained deletions in either one or both of the two segments of rvWF amino acid sequence flanking the loop region (defined as the amino acid sequence between cysteine 509 and cysteine 695. Some of the mutant molecules had complete or partial deletions of one or both of two short segments of sequence, Mohri, H. et al., *J. Biol. Chem.*, 263(34), 17901–17904 (1988), that are involved in effecting binding of vWF to GPIbα- residues 474 to 488 and also 694 to 708, as denoted by the cross hatched boxes in FIG. 2.

The interaction the mutant molecules with GPIbα was evaluated using an assay (Sugimoto, M. et al., *Biochemistry*, 30, 5202–5209 (1991)) based on inhibition of binding of antibody LJ-Ib1 to platelets. The corresponding IC$_{50}$ values (concentration of fragment required to inhibit 50% of antibody binding) are presented in Table 2 (no modulator) and Table 3 (botrocetin added). The lowest IC$_{50}$ values, indicating the greatest binding affinity, were obtained with mutant molecules possessing a complete deletion of the sequence on the amino terminal side of the loop. Among the reduced and alkylated mutant molecules containing deletions, all but two of the molecules demonstrated an affinity for GPIbα similar to or greater than that of rvWF$^{441-733}$. Two species (in reduced and alkylated form) which possessed complete deletions of the sequence on the carboxyl terminal side of cysteine 695 (rvWF$^{508-696}$, rvWF$^{441-696}$) had a greatly reduced ability to inhibit LJ-Ib1 binding to platelets (Table 2).

TABLE 2

Inhibition of LJ-Ib1 binding to Platelets by recombinant vWF fragments in the absence of modulators

| Designation | (Oxidized) IC50 (μM) | n | (Reduced/alkylated) IC (μM) | n |
|---|---|---|---|---|
| rvWF$^{441-733}$ | 3–5 | 6 | 0.07–0.3 | 6 |
| rvWF$^{492-733}$ | 1.2–4 | 3 | 0.04–0.05 | 2 |
| rvWF$^{508-733}$ | 0.1–0.3 | 4 | 0.02–0.03 | 3 |
| rvWF$^{441-704}$ | 2.6–3.2 | 2 | 0.03–0.04 | 2 |
| rvWF$^{441-700}$ | 2.0–3.1 | 2 | 0.5 | 2 |
| rvWF$^{441-696}$ | 1.0–1.3 | 3 | >4 | 3 |
| rvWF$^{508-704}$ | 0.6 | 1 | 0.09 | 1 |
| rvWF$^{508-696}$ | 0.4–0.7 | 2 | >4 | 2 |

The values reported represent the range of results observed in the indicated number of experiments.

TABLE 3

Inhibition of LJ-Ib1 binding to Platelets by recombinant vWF fragments in the Presence of Botrocetin

| Designation | (Oxidized) IC50 (mM) | n | (Reduced/alkylated) IC (mM) | n |
|---|---|---|---|---|
| rvWF$^{441-733}$ | 13–25 | 3 | 4–24 | 3 |
| rvWF$^{492-733}$ | 36 | 1 | 28 | 1 |
| rvWF$^{508-733}$ | 2.6 | 1 | 17 | 1 |
| rvWF$^{441-704}$ | 6 | 1 | 6 | 1 |
| rvWF$^{441-700}$ | 8 | 1 | 30–36 | 2 |
| rvWF$^{441-696}$ | 33 | 1 | 20 | 1 |
| rvWF$^{508-704}$ | 6 | 1 | 31 | 1 |
| rvWF$^{508-696}$ | 200 | 2 | 51 | 1 |

The values reported represent the range of results observed in the indicated number of experiments.

The integrity of the 185-residue loop between cysteine residues 509 and 695 is demonstrated to make a significant contribution to GPIb-binding function. This result is supported by the observation, when the intrachain Cys$^{509}$-Cys$^{695}$ bond is oxidized, complete deletion of the sequences flanking the disulfide loop, on both the amino and carboxyl terminal sides thereof, has no deleterious effect on the interaction of the loop with GPIbα. These results imply that none of the residues within the amino acid sequences 441–508 and 696–733 of vWF subunit is strictly necessary for expression of the GPIbα-binding by vWF-derived antithrombotic polypeptides. With regard to the potential use of isolated recombinant fragments of vWF as therapeutic antithrombotic agents, effective structures that achieve functional inhibition of the vWF-binding site on GPIbα include the cyclic 508–696 molecule containing the Cys$^{509}$-Cys$^{695}$ disulfide bond, and also a residue 508–704 polypeptide in both reduced and oxidized form.

Example 16
Behavior of Oxidized (at Cysteine) and Reduced Forms of Residue 441–733 vWF Fragment in the Presence of Botrocetin The interaction of rvWF$^{441-733}$ with GPIbα was measured by the ability of rvWF$^{441-733}$ to inhibit the binding of an anti-GPIbα monoclonal antibody, LJ-IB1, to platelets. This assay, previously described in detail, (Sugimoto, M. et al., *Biochemistry*, 30, 5202–5208 (1991)) offers the advantage that the binding of LJ-Ib1, unlike that of native vWF, is not dependent on the presence of modulators, like ristocetin or botrocetin. Binding by vWF$^{441-733}$ to GPIbα is thought to block the region of GPIbα to which LJ-Ib1 binds.

Two forms of rvWF$^{411-733}$ were utilized in these experiments; an oxidized form retaining the Cys$^{509}$-Cys$^{695}$ disulfide bond (as a p5E construct) and a reduced and alkylated form of rvWF$^{441-733}$ lacking the disulfide bond.

The results of the experiments are shown in FIGS. 3A and 3B. In the absence of modulator the reduced and alkylated form of rvWF$^{441-733}$ interacted with GPIbα with a much greater affinity than the oxidized form (the concentration of reduced and alkylated rvWF$^{441-733}$ required to inhibit 50% of LJ-Ib1 binding (IC$_{50}$) was more than ten fold lower than the amount of oxidized rvWF$^{441-733}$ required to produce a similar inhibition of LJ-Ib1 binding, FIG. 3A). The modulator botrocetin had a dramatic effect on the GPIbα binding affinity of both forms of rvWF$^{441-733}$. The effect of botrocetin was proportionally much greater for the oxidized species, however, so that, in the presence of botrocetin, the oxidized form inhibited LJ-Ib1 binding to platelets with an affinity similar to that of the reduced and alkylated form (FIG. 3B).

The Cys$^{509}$-Cys$^{695}$ bond, therefore, contributes to the stabilization of a conformation of native vWF in solution that prevents its interaction with circulating platelets but allows expression of full binding activity in the presence of appropriate modulators.

Example 17

Polypeptide Purification

The recombinant vWF residue 441–733 fragments were purified to homogeneity both in oxidized form or after reduction and alkylation of the two p5E cysteine residues (509, 695), and the two forms could be differentiated by reversed phase HPLC on the basis of a distinct retention time. They presented also different mobility by SDS-polyacrylamide gel electrophoresis.

Deposit of Hybridomas and Strains Useful in Practicing the Invention

Deposits of biologically pure cultures of the following hybridomas/strains were made under the Budapest Treaty with the American Type Culture Collection, 12301 Parklawn Drive, Rockville, Md. The accession numbers indicated were assigned after successful viability testing, and the requisite fees were paid.

Access to said cultures will be available during pendency of the patent application to one determined by the Commissioner of the United States Patent and Trademark Office to be entitled thereto under 37 C.F.R. §1.14 and 35 U.S.C. §122, or if and when such access is required by the Budapest Treaty. All restriction on availability of said cultures to the public will be irrevocably removed upon the granting of a patent based upon the application and said cultures will remain permanently available for a term of at least five years after the most recent request for the furnishing of samples and in any case for a period of at least 30 years after the date of the deposits. Should the cultures become nonviable or be inadvertently destroyed, they will be replaced with viable culture(s) of the same taxonomic description.

| Hybridomas or Strains | ATCC No. | Deposit Date |
| --- | --- | --- |
| E. coli p5E BL21 (DE3) 96.3 | ATCC 68406 | 9/19/90 |
| E. coli XS127 96.4 | ATCC 68407 | 9/19/90 |
| Murine hybridoma LJ-Ib1 (TSRI 138.5) | ATCC HB10940 | 12/3/91 |

What is claimed is:

1. A polypeptide which is capable of inhibiting binding of von Willebrand factor (vWF) to platelets and which is selected from the group consisting of:

(A) a polypeptide comprising an amino acid sequence that corresponds to the amino acid sequence of that fragment of mature von Willebrand factor subunit having its amino terminus at about $Cys^{509}$ and its carboxy terminus at about $Cys^{695}$ and in which the residue Cys$^{509}$ and the residue Cys$^{695}$ are joined by an intrachain disulfide bond, said polypeptide being a modified form of said fragment in that said polypeptide does not include said cysteine residues are modified such that they are incapable of forming a disulfide bond;

(B) a polypeptide comprising: (i) an amino acid sequence that corresponds to said modified form of said fragment of (A); and (ii) an amino acid sequence that corresponds to the amino acid sequence of that fragment of mature vWF subunit having its amino terminus at about Arg$^{441}$ and its carboxy terminus at about Tyr$^{508}$, or a subfragment or combination of subfragments thereof; wherein said sequences of (i) and (ii) are linked by a covalent bond between the amino terminus of said fragment of (i) and the carboxy terminus of said fragment of (ii); and (C) a polypeptide comprising: (i) an amino acid sequence that corresponds to said modified form of said fragment of (A); and (ii) an amino acid sequence that corresponds to the amino acid sequence of that fragment of mature vWF subunit having its amino terminus at about Asp$^{696}$ and its carboxy terminus at about Val$^{733}$, or a subfragment or combination of subfragments thereof; wherein said sequences of (C)(i) and (C)(ii) are linked by a covalent bond between the carboxy terminus of said fragment of (C)(i) and the amino terminus of said fragment of (C)(ii).

2. A polypeptide according to claim 1 wherein the cysteine residues at positions 509 and 695 are in reduced and alkylated form.

3. A polypeptide according to claim 2 wherein an acetamide group is covalently bonded to the sulfur atom of said cysteine residues.

4. A polypeptide comprising a fragment of mature von Willebrand factor subunit selected from the group consisting of Arg$^{441}$ to Asp$^{709}$, Arg$^{441}$ to Pro$^{704}$, Arg$^{441}$ to Glu$^{700}$, Arg$^{441}$ to Asp$^{696}$, Gln$^{475}$ to Val$^{733}$, Thr$^{492}$ to Val$^{733}$, Tyr$^{508}$ to Val$^{733}$, Tyr$^{508}$ to His$^{709}$, Tyr$^{508}$ to Pro$^{704}$, and Tyr$^{508}$ to Glu$^{700}$, wherein cysteine residues Cys$^{509}$ and Cys$^{695}$ of said fragments are joined by an intrachain disulfide bond, said polypeptide being a modified form of said fragment in that said polypeptide does not include said disulfide bond.

5. A polypeptide according to claim 4 wherein the cysteine residues at positions 509 and 695 are in reduced and alkylated form.

6. A polypeptide according to claim 4 having an amino terminus at about Tyr$^{508}$ and a carboxy terminus at about Pro$^{704}$ wherein the cysteine residues at positions 509 and 695 are in reduced and alkylated form.

7. A polypeptide which is capable of inhibiting binding of von Willebrand factor (vWF), to platelets and which is selected from the group consisting of:

(A) a polypeptide comprising an amino acid sequence that corresponds to the amino acid sequence of that fragment of mature von Willebrand factor subunit having its amino terminus at about Cys$^{509}$ and its carboxy terminus at about Cys$^{695}$ and in which the amino acid residue Cys$^{509}$ and the amino acid residue Cys$^{695}$ are joined by an intrachain disulfide bond, said polypeptide being a modified form of said fragment in that said polypeptide does not include said disulfide bond and said amino acid residues are other than cysteine amino acid residues;

(B) a polypeptide comprising: (i) an amino acid sequence that corresponds to said modified form of said fragment of (A); and (ii) an amino acid sequence that corresponds to the amino acid sequence of that fragment of mature vWF subunit having its amino terminus at about Arg$^{441}$ and its carboxy terminus at about Tyr$^{508}$, or a subfragment or combination of subfragments thereof; wherein said sequences of (i) and (ii) are linked by a covalent bond between the amino terminus of said fragment of (i) and the carboxy terminus of said fragment of (ii); and (C) a polypeptide comprising: (i) an amino acid sequence that corresponds to said modified form of said fragment of (A); and (ii) an amino acid sequence that corresponds to the amino acid sequence of that fragment of mature vWF subunit having its amino terminus at about Asp$^{696}$ and its carboxy terminus at about Val$^{733}$, or a subfragment or combination of subfragments thereof; wherein said sequences of (C) (i) and (C) (ii) are linked by a covalent bond between the carboxy terminus of said fragment of (C) (i) and the amino terminus of said fragment of. (C) (ii).

8. A polypeptide comprising a fragment of mature von Willebrand factor subunit selected from the group consisting of Arg$^{441}$ to Asp$^{709}$, Arg$^{441}$ to Pro$^{704}$, Arg$^{441}$ to Glu$^{700}$, Arg$^{441}$ to Asp$^{696}$, Gln$^{475}$ to Val$^{733}$, Thr$^{492}$ to Val$^{733}$, Tyr$^{508}$ to Val$^{733}$, Tyr$^{508}$ to His$^{709}$, Tyr$^{508}$ to Pro$^{704}$, and Tyr$^{508}$ to Glu$^{700}$, wherein cysteine residues Cys$^{509}$ and Cys$^{695}$ of said fragments are joined by an intrachain disulfide bond, said polypeptide being a modified form of said fragment in that amino acid residues other than cysteine are present at positions 509 and 695 of the polypeptide.

9. A polypeptide according to claim 8 having an amino terminus at about Tyr$^{508}$ and a carboxy terminus at about Pro$^{704}$.

10. A polypeptide according to claim 8 wherein the amino acid residues at positions 509 and 695 are glycine residues.

11. A DNA sequence encoding a polypeptide according to claim 8.

* * * * *

UNITED STATES PATENT AND TRADEMARK OFFICE
CERTIFICATE OF CORRECTION

PATENT NO. : 5,900,476
DATED : May 4, 1999
INVENTOR(S) : Zaverio M. Ruggeri and Jerry L. Ware It is certified that error appears in the above-indentified patent and that said Letters Patent is hereby corrected as shown below:

On the title page, item 54 and column 1, the title should read --THERAPEUTIC DOMAINS OF VON WILLEBRAND FACTOR--. Column 57, line 3, delete "said polypeptide does not include".

Signed and Sealed this

Ninth Day of November, 1999

Attest:

Q. TODD DICKINSON

Attesting Officer

Acting Commissioner of Patents and Trademarks